United States Patent [19]

Lundin et al.

[11] Patent Number: 5,705,345
[45] Date of Patent: Jan. 6, 1998

[54] METHODS AND KITS FOR PREPARING NUCLEIC ACIDS USING CYCLODEXTRIN

[75] Inventors: Arne Lundin, Dalaro, Sweden; John George Anson; Michael Kenneth Kenrick, both of Cardiff, Wales

[73] Assignee: Amersham International plc, Buckinghamshire, United Kingdom

[21] Appl. No.: 645,688

[22] Filed: May 14, 1996

Related U.S. Application Data

[63] Continuation-in-part of Ser. No. 347,228, Nov. 23, 1994, Pat. No. 5,558,986, which is a continuation of Ser. No. 75,484, filed as PCT/GB92/00056, Jan. 10, 1992, Pat. No. 9,200,056.

[30] Foreign Application Priority Data

Jan. 10, 1991 [GB] United Kingdom ............ 9100551

[51] Int. Cl.$^6$ ............ C12Q 1/68; C12P 19/34; C07H 21/04
[52] U.S. Cl. ............ 435/6; 435/91.2; 435/810; 536/25.4; 536/25.41; 536/25.42
[58] Field of Search ............ 435/6, 91.2, 810; 536/25.4, 25.41, 25.42

[56] References Cited

U.S. PATENT DOCUMENTS

| | | | |
|---|---|---|---|
| 4,357,468 | 11/1982 | Szejtli et al. | 536/56 |
| 4,772,397 | 9/1988 | Szucs et al. | 210/635 |
| 4,917,956 | 4/1990 | Rohrbach | 428/423.1 |
| 5,032,503 | 7/1991 | Khanna et al. | 435/7.6 |
| 5,558,986 | 9/1996 | Lundin | 435/4 |

FOREIGN PATENT DOCUMENTS 0 301 847  2/1989  European Pat. Off.

OTHER PUBLICATIONS

Baselski et al., Abstract presented at 92nd General Meeting of the American Society for Microbiology, May 1992.
Loeffelholz et al., J. Clin. Microbiol. 30(11), 2847–2851 (Nov. 1992).

*Primary Examiner*—Kenneth R. Horlick
*Attorney, Agent, or Firm*—Wenderoth, Lind & Ponack

[57] ABSTRACT

A method of preparing nucleic acids by obtaining an impure nucleic acid preparation, treating said preparation with phenol and adding a cyclodextrin to the treated preparation to neutralize the phenol.

17 Claims, 22 Drawing Sheets

METHODS AND KITS FOR PREPARING NUCLEIC ACIDS USING CYCLODEXTRIN

This is a continuation-in-part of Ser. No. 08/347,228, filed Nov. 23, 1994, U.S. Pat. No. 5,558,986; which is a continuation of Ser. No. 08/075,484, filed Jun. 11, 1993, now abandoned; which is the U.S. national stage of PCT/GB92/00056, filed Jan. 10, 1992.

The present invention relates to a method for extraction of intracellular components including intracellular metabolites. The invention addresses the problem that many substances used for extracting components from cells interfere with assays or other processing steps performed on the extracted components. The invention uses cyclodextrins to neutralise the extracting substances. In one example according to the invention, the intracellular metabolite is adenosine triphosphate (ATP) which can, after neutralisation of the extractants, be assayed using a firefly luciferin-luciferase reaction. In another example, the intracellular components are nucleic acids which can, after neutralisation of the extractants, be amplified or further processed in other ways.

General aspects of extraction of intracellular components

The assay of intracellular components in biological samples is often performed by enzymatic methods. Such methods require: 1) Release of the components from the cells to make the components available to enzyme systems added in the assay. 2) Inactivation of enzymes from the cells that may act on the components during preparation, storage or assay of extracts. Extraction of the intracellular components involves opening of cell walls and membranes and release of the entire metabolite pools into the surrounding medium. Within the cells the metabolite pools often have turn-over times around a few seconds due to the action of the intracellular enzymes. As soon as an extractant starts to affect membrane integrity the enzyme systems of the cell try to counteract the resulting effects. Thus considerable changes of metabolite levels may take place during an extraction which takes time. This would obviously result in completely erroneous data on intracellular metabolite levels even using the best enzymatic assays. The only way to avoid the problem is to use extractants that rapidly open up the cell membranes and simultaneously inactivate all enzymes that act on the intracellular components. Enzyme inactivation is therefore an inherent property of all reliable extractants. The presence of a cell wall protects the cell from the extractant and makes bacterial, fungal and algal cells particularly difficult to extract. Thus strong acids with chaotropic anions like trichloroacetic acid (TCA) or perchloric acid (PCA) have frequently been used for the extraction of these types of cells. Such agents are strongly enzyme inactivating and inevitably interfere with enzymatic assays unless extracts are highly diluted before the assay. Dilution of the extracts makes it difficult to assay low concentrations of metabolites.

The more rapid the turn-over rate of the intermediate metabolite the higher is the requirement for immediate inactivation of cellular enzymes at the addition of the extractant. From this point of view ATP is one of the most difficult intracellular metabolites to extract. In all cells ATP is the means by which energy is transferred from energy yielding to energy requiring reactions. Thus many ATP converting enzymes (kinases and ATPases) exist and have high activities. Even a slight damage of membrane integrity, e.g. by an extractant, results in a rapid loss of intracellular metabolites and ions. As the cell tries to compensate for these events large quantities of ATP are consumed. One object of the work leading to this invention was to develop a reliable extraction method for microbial ATP compatible with the firefly luciferase assay. The rapid turn-over of ATP and the presence of thick cell walls in microbial cells make it likely that an extraction method for microbial ATP will work also for most other intracellular metabolites in any type of cell (unless the extractant by itself degrades the metabolite). Furthermore in the firefly luciferase assay of ATP the rate of the reaction is measured, i.e. the firefly assay is an example of kinetic assays. Thus any inhibitor added during or after the extraction will affect the assay. The activity of firefly luciferase is inhibited by a wide variety of compounds including simple salts. Firefly luciferase also has a narrow pH optimum. Thus an extraction method that works with the firefly assay is likely to work with most other enzymatic assays. This is particularly true for any end-point assay for which an inhibition can be compensated simply by extending the assay time.

Extraction of DNA and RNA

The extraction of nucleic acids from biological material forms a critical first step in many molecular biology studies. The extracted DNA or RNA is required as a substrate or template for subsequent enzymatic reactions, and hence must be biologically active. Commonly, DNA from cells or tissue is used for the amplification of specific sequences by the polymerase chain reaction (PCR) or cleavage with restriction enzymes for gene cloning or identification. The purification of genomic DNA from cells or tissue for subsequent use in gene analysis experiments conventionally involves cell lysis to release all cellular components, followed by selective digestion of proteins and RNA with specific degradative enzymes. After separation from proteinaceous material and other contaminants the DNA sample is relatively pure and functionally active. The separation step is conventionally performed by extraction with organic solvents followed by precipitation of the DNA with alcohol (J. Sambrook, E. F. Fritsch and T. Maniatis, Molecular Cloning—A Laboratory Manual, second edition, Cold Spring Harbor Laboratory Press, 1989). Methods have been described where functionally active genomic DNA can be prepared without specific removal of contaminating protein, for example by ethanol precipitation of cell lysates (H. Xu, A. M. Jevnikar and E. Rubin-Kelly, Nucleic Acids Research 18, 4943). The critical contaminant therefore appears to be the extractant used, which is conventionally a detergent. Removal of the detergent can therefore be sufficient to allow the DNA to be used for subsequent reactions. However, conventionally detergent removal still requires a separation step, with the subsequent increase in preparation time and potential reduction in yield. A homogeneous system without any separation steps would therefore have significant advantages over current methods.

Present situation with respect to extraction and assay of microbial ATP

In rapid microbiology the firefly luciferase assay of ATP is frequently used for biomass estimations. The intracellular ATP concentration is similar in all cells and the amount of ATP per cell is approximately proportional to the intracellular volume. Bacteria contain approx. $10^{-18}$ moles of ATP per cell while fungi and algae contain considerably more ATP per cell. With simple light measuring instruments and firefly luciferase reagents $10^{-15}$ moles of ATP is easily detected in a 1 ml volume. This corresponds to approx. $10^3$ bacterial cells. Bacterial ATP in a biological specimen can be extracted by adding an equal volume of 2.5% trichloroacetic acid. However, to avoid interference from trichloroacetic acid with the luciferase reaction a sample volume larger than 0.01 ml cannot be used in a final assay volume of 1 ml. Thus the detection limit in the biological specimen is $10^5$ cells/ml.

Neutralisation of the acid improves the situation somewhat but most of the inhibition comes from the chaotropic anion of the acid.

The situation described above has led to a continuous search for alternative extraction methods. Among alternative extractants the quaternary ammonium compounds, e.g. benzalkonium chloride, have been suggested (S. Aséhn, A. Lundin, L. Nilsson and A. Thore, Detection of bacteriuria by a simplified luciferase assay of ATP. Proceedings: International Symposium on Analytical Applications of Bioluminescence and Chemiluminescence, pp. 438–445, State Printing & Publishing, Inc., Westlake Village, Calif., 1979). However, quaternary ammonium compounds inactivate firefly luciferase to give a gradual decay of the light emission after addition of the extract to the firefly reagent. Such a gradual decrease of the luciferase activity during the light measurement makes it almost impossible to calibrate the assay by adding a known amount of ATP (the internal standard technique). In the above paper it was stated that the inactivation effect could be partially counteracted by addition of bovine serum albumin. However, in later efforts to optimise this procedure it was found that the concentrations of albumin needed (2.5–10%) to completely avoid the inactivation of luciferase by quaternary ammonium compounds resulted in a strong inhibition of the luciferase reaction (A. Lundin, Extraction and automatic luminometric assay of ATP, ADP and AMP. In Analytical Applications of Bioluminescence and Chemiluminescence, L. Kricka, P. Stanley, G. Thorpe and T. Whitehead, Eds., pp. 545–552, Academic Press, New York, 1984). The important finding was, however, that the luciferase inactivating effect of quaternary ammonium compounds could be neutralised although albumin was not ideal for the purpose. An alternative neutralising agent for quaternary ammonium compounds was later found to be nonionic surfactants, e.g. Tween 20, Tween 60, Tween 80, Polyoxyethylene ether W1 and Triton X-100 (W. J. Simpson and J. R. M. Hammond, EP 309184). S. Kolehmainen and V. Tarkkanen have proposed (GB 16004249) the use of nonionic surfactants as extractants in their own right. Nonionic surfactants counteract the gradual inactivation of luciferase by quaternary ammonium compounds and are not by themselves strongly inhibitory in the luciferase reaction. However, a considerable inhibition of the luciferase reaction is obtained at the addition of quaternary ammonium compounds even in the presence of nonionic surfactants (cf. Example 1). Thus no system has been described that obviates both problems with quaternary ammonium compounds, i.e. inhibition and inactivation of luciferase.

Considerations underlying the invention as applied to ATP

Transport of samples to a laboratory obviates the major advantage of the firefly ATP assay in rapid microbiology, i.e. the fact that analytical results are provided within minutes. A ma3or potential market for such assays is actually field testing under non-laboratory conditions using personnel with little or no training in biochemical analysis. Under such conditions assays would normally involve low numbers of samples in each series and would have to be performed with reagents stored at ambient temperature and with low-price and simple instrumentation. Analytical procedures would have to involve a minimum number of very simple steps using reagents with a format suitable for single assays. Prototype analytical systems for such assays based on dipstick technology have been described (A. Lundin, ATP assays in routine microbiology: From visions to realities in the 1980s, in ATP Luminescence: Rapid Methods in Microbiology, P. E. Stanley, B. J. McCarthy and R. Smither, Eds., The Society for Applied Bacteriology Technical Series 26, Blackwell Scientific Publications, pp. 11–30, Oxford, 1989).

A serious problem in the development of commercial reagent kits for the firefly assay would be that the ATP standard is less stable than the firefly luciferin-luciferase reagent. It is unlikely that an ATP standard can be stored for prolonged times at ambient temperatures can be developed. Reconstitution and dispensing of the ATP standard in the assay represent further problems. An ATP standard solution would have to be added in an accurate volume $\leq 1\%$ of the total assay volume (A. Lundin, Clinical Applications of Luminometric ATP monitoring. Thesis from Karolinska Institute, 1990). Accurate pipetting of microliter volumes by untrained personnel under field testing conditions would be very difficult to achieve. The price of automatic equipment would be prohibitive in this market. Even if all the above problems could be solved the internal standard technique makes it necessary to perform two light measurements, i.e. before and after addition of the ATP standard. Thus from several points of view it would be highly advantageous if the assay could be performed without the use of ATP standards. This could be achieved using standardised firefly reagents with an essential stable light emission always having the same relation to the ATP concentration in all samples. Lyophilised firefly reagents that can be stored for years with no loss of activity having an essentially stable light emission during several minutes have been commercially available since the late 1970s (A. Lundin, Clinical Applications of Luminometric ATP Monitoring, Thesis from the Karolinska Institute, 1990). Systems for simple automatic calibration of the light response of light measuring instruments also represent well established technology. The only remaining problem would be to assure that addition of extracts of biological material affects the luciferase activity neither by inactivation (resulting in a decay of the light emission) nor inhibition (resulting in a decreased but stable light emission) during the light measurement.

Very potent extractants that rapidly penetrate the cell wall and inactivate the intracellular enzymes have to be used with microbial cells. The interference with enzymatic analysis from such extractants can be obviated by: 1) Dilution of extracts (resulting in a reduced sensitivity of the assay). 2) Removal of the extractant from the extract (most likely resulting in time-consuming and laborious procedures). 3) Neutralisation of the extractant by including a neutralising agent in the assay buffer. The last suggestion is obviously the most attractive alternative. The requirement for very potent extractants also makes it difficult to achieve. The situation is not simplified by the fact that the neutraliser has to be relatively inert with no effects on luciferase activity.

The overall aim of this aspect of the present invention can be stated as the development of a combination of extractants and neutralisers that causes neither inactivation of luciferase nor inhibition of the luciferase reaction. Only by achieving both these goals convenient and reliable ATP assays can be performed under field testing conditions, i.e. without using ATP standards.

Neutralisation of an extractant can be achieved by performing a chemical reaction to destroy the extractant. The simplest example would be the neutralisation of an acid extractant by addition of a base. However, an exact pH adjustment would be required (strong buffers are inhibitory) and would not be practicable in many situations. Furthermore the best acid extractants have chaotropic anions, which are strongly inhibitory even at neutral pH. Even an increased ionic strength reduces luciferase activity. An alternative approach would be to destroy the extractant by forming a new non-inhibitory compound by a chemical reaction. However, this would most likely have to involve highly reactive reactants that would be likely to inhibit or inactivate enzymes.

The most attractive approach would be to form a complex between the extracting molecule and a neutralising molecule. The use of nonionic surfactants to neutralise quaternary ammonium compounds (a type of cationic surfactants) is an example of this approach (W. J. Simpson and J. R. M. Hammond, European Patent Application 88308677.9). Actually nonionic surfactants neutralise the inactivation effect on firefly luciferase of all types of ionic surfactants (cationic, anionic and zwitterionic) as shown in Example 1. However, in the presence of nonionic surfactants all the ionic surfactants give an inhibitory effect at much lower concentrations than those causing inactivation. This may be due to a poor association between nonionic and ionic surfactants or to an inhibition from the complex between the two types of surfactants.

Regardless of explanation the inhibition is likely to vary from sample to sample depending on the level of biological material that may bind extractants of the ionic surfactant type. Thus it would be necessary to use ATP standards in each assay. A further disadvantage of nonionic surfactants as neutralisers is that not all enzymes are as resistant as firefly luciferase to these agents.

The ideal compound for neutralising extractants would have a high association constant for the extractant. Ideally it would form an inclusion complex so that the part of the extractant molecule that inactivates enzymes is surrounded by a protective layer. Obviously the neutralising compound should be as inert with enzymes as possible and should not irreversibly bind intracellular metabolites that are of analytical interest. Some surfactants, e.g. the quaternary ammonium compounds, have been found to be useful extractants (A. Lundin, Extraction and automatic luminometric assay of ATP, ADP and AMP). In Analytical Applications of Bioluminescence and Chemiluminescence, L. Kricka, P. Stanley, G. Thorpe and T. Whitehead, Eds., pp 545–552, Academic Press, New York, 1984). A common feature of all surfactant molecules is a hydrophobic tail. The formation of an inclusion complex in which the hydrophobic tail is buried in a complex with a hydrophilic outer surface would be ideal. This might be achieved using a neutralising agent forming micelles. However, enzymes added in the analytical procedure may become incorporated into the micelles resulting in a changed activity. Furthermore an interaction between the enzymes and the extractants within the micelle can not be excluded. The ideal neutralising agent for surfactants would be a water-soluble compound with a hydrophilic outer surface not likely to bind to enzymes and a hydrophobic cave with an appropriate size to form inclusion compounds with surfactants.

Properties of cyclodextrins

Cyclodextrins are doughnut-shaped molecules consisting of 6, 7 or 8 glucose units ($\alpha$-, $\beta$ and y-cyclodextrin). The internal diameter of the ring is 6 Å, 7.5 Å and 9.5 Å, respectively. The interior of the ring binds the hydrophobic tails of molecules as e.g. surfactants. The resulting inclusion complexes are generally formed with a 1:1 stoichiometry between surfactant and cyclodextrin. the association constants with $\alpha$-, $\beta$ and y-cyclodextrin depend on the size and chemical properties of the hydrophobic tail of the surfactant. The association constant with surfactants is generally in the range $10^3$–$10^4$ but may be as high as $5 \times 10^4$ dm$^3$ mol$^{-1}$ (L Satake, T. Ikenoue, T. Takeshita, K. Hayakawa and T. Maeda, Conductometric and potentiometric studies of the association of $\alpha$-cyclodextrin with ionic surfactants and their homologs, Bull. Chem. Soc. Jpn. 58, 2746–2750, 1985; R. Palepu and J. E. Rickardson, Binding constants of $\beta$-cyclodextrin/surfactant inclusion by conductivity measurements, Langmuir 5, 218–221, 1989; I. Satake, S. Yoshida, K. Hayakawa, T. Maeda and Y. Kusumoto. Conductometric determination of the association constants of $\beta$-cyclodextrain with amphiphilic ions, Bull. Chem. Soc. Jpn. 59, 3991–3993, 1986; T. Okubu, Y. Maeda and H. Kitano, Inclusion process of ionic detergents with cyclodextrins as studied by the conductance stopped-flow method, J. Phys. Chem. 93, 3721–3723, 1989; R. Palepu and v. C. Reinsborough, Surfactant-cyclodextrin interactions by conductance measurements, Can. J. Chem. 66, 325–328, 1988). The outer surface of the cyclodextrins is hydrophilic and is unlikely to interact with most enzymes. Furthermore the cyclodextrins are water soluble, although they can be immobilised, e.g. by polymerisation or by attachment to a solid or particulate surface. The use of cyclodextrins to remove surfactants from surfaces and solutions have been described. (P. Khanna and R. Dworschack, European Patent Application EP 301,847). According to this patent application surfactants can be removed from solutions by immobilised cyclodextrins. The possibility not to remove but to neutralise the effect of the surfactants by forming inclusion complexes was not evaluated. P. Khanna et al. EP 286367 describe the use of cyclodextrins to neutralise surfactants used as stabilisers of peptide fragments prior to assay. In a review various applications of cyclodextrins in diagnostics have been described (J. Szejtli, Cyclodextrins in diagnostics, Kontakte (Darmstadt) 1988 (1), 31–36). The use of cyclodextrins to neutralise surfactants added as extractants to release intracellular metabolites has not been previously described.

DESCRIPTION OF THE INVENTION

According to the present invention there is provided a method of preparing an extract of an intracellular component by providing a solution containing an intracellular component and a substance used for extracting the component, characterised by contacting the solution with a cyclodextrin or a cyclodextrin derivative of an appropriate type and in an appropriate amount to neutralise the extracting substance. The nature of the intracellular component is not material to the invention. Examples are nucleic acids such as DNA and RNA and other intracellular metabolites as discussed above including ATP.

The term "neutralise" as used herein does not refer to adjustment of pH to 7.0. Rather, neutralising the extractants involves reducing/obviating/overcoming the interference that the extractant would otherwise cause in subsequent processing of the extracted intracellular component.

The function of the cyclodextrin or derivative is to neutralise the extracting substance or extractant. As discussed above, this can be done in principle by destroying the extractant. If the cyclodextrin or derivative is used in an insoluble form, the complex formed with the extractant is also insoluble and is readily physically removed from the remaining solution. More usually, the cyclodextrin or derivative is used in solution and neutralises the extractant by forming a complex with it. It is then possible, but usually not necessary or desirable, to remove that complex from the solution. While complete neutralisation of the surfactant is preferred, the invention also envisages conditions which result in partial neutralisation; these should significantly reduce interference by the extractant in any subsequent assay, amplification or further processing.

In another aspect, the invention provides a kit for the extraction and assay of ATP in biological specimens by the method herein described, characterised in that the kit comprises the following components:
a) an extracting substance (stored separately from the other components),
b) a cyclodextrin,
c) a firefly luciferase reagent,
d) an assay buffer.

Preferably the extracting substance is dried on or in a carrier that picks up a sample of suitable size when contacted with a fluid specimen; the cyclodextrin is dissolved in the assay buffer; and the firefly luciferase reagent is dried on or in a carrier that can release the reagent into the assay buffer.

Any type of extractant and any type of cyclodextrin or cyclodextrin derivative can be used provided that the association between extractant and cyclodextrin is strong enough to avoid inhibition or inactivation of the enzymes used in the analytical procedure. The extractant is preferably a surfactant which is preferably contacted with α-, β- or γ-cyclodextrin depending on which cyclodextrin binds the surfactant most effectively. Cationic, anionic and zwitterionic surfactants can be neutralised by cyclodextrins (Example 1). An idea of which cyclodextrin is likely to be the most suitable for a particular surfactant can often be obtained from published association constants (cf. references above). For a particular application optimisation of type and concentration of extractant and cyclodextrin can be performed as described in the examples (cf. below). The cyclodextrin is preferably used in excess of the surfactant on a molar basis considering the stoichiometry of the inclusion complex that is formed. The cyclodextrin can be added at any step in the analytical procedure after completion of the extraction but always before or simultaneously with the addition of the enzymes involved in the assay.

The major advantage of cyclodextrins as neutralisers of extractants in the firefly ATP assay is that analytical conditions can be found under which the light emission is neither affected by inhibition nor by inactivation from the extractant/neutraliser complex. This is achieved by using an extractant/cyclodextrin combination with a high binding constant. With previously available neutralisers, e.g. non-ionic surfactants used to neutralise quaternary ammonium compounds (W. J. Simpson and J. R. M. Hammond, EP 309184), inactivation but not inhibition could be avoided. Cyclodextrins are unlikely to inhibit or inactivate enzymes and have actually been used as stabilisers of enzyme reagents (J. Szejtli, Cyclodextrins in diagnostics, Kontakte (Darmstadt) 1988 (1), 31–36). An apparent inhibition effect on the light emission in the luciferase reaction from β-cyclodextrin was found (Example 1). However, it was shown that this effect was due to the formation of a D-luciferin/β-cyclodextrin complex. The problem could be obviated by increasing the concentration of D-luciferin. If an apparent inhibition is found in any other assay it is recommended to optimise the concentrations of all cofactors in the presence of the cyclodextrin that is to be used.

Based on the present invention the combination of extractants, cyclodextrins and firefly reagents in kit format for the extraction and assay of intracellular ATP in various types of microorganisms or in special types of samples is a simple task. Analytical systems suitable for field use can be developed by combining the present invention with the previously described dipstick technology (A. Lundin, ATP assays in routine microbiology: From visions to realities in the 1980s, in ATP Luminescence: Rapid Methods in Microbiology, P. E. Stanley, B. J. McCarthy and R. Smither, Eds., The Society for Applied Bacteriology Technical Series 26, Blackwell Scientific Publications, pp. 11–30, Oxford, 1989). In such systems a predetermined sample volume would be brought in contact with an extractant (e.g. a quaternary ammonium compound dried on a matrix), the extracted sample and a firefly reagent (also dried on a matrix) would subsequently be dissolved in a predispensed buffer containing a suitable cyclodextrin. The light emission from the cuvette containing extracted ATP, extractant neutralised with cyclodextrin, firefly reagent and buffer could be directly measured in a portable instrument. With standardised reagents and instruments it would not be necessary to calibrate each assay individually with an ATP standard. Thus the entire procedure would be completed within a minute without using a pipette.

In the following the invention will be further illustrated by examples from the extraction and assay of intracellular ATP in microorganisms by the firefly luciferase method. The use of quaternary ammonium compounds for the extraction of microbial ATP is well established (A. Lundin, Extraction and automatic luminometric assay of ATP, ADP and AMP. In Analytical Applications of Bioluminescence and Chemiluminescence, L. Kricka, P. Stanley, G. Thorpe and T. Whitehead, Eds. pp. 545–552, Academic Press, New York, 1984). Quaternary ammonium compounds are cationic surfactants. In the examples it will be shown that anionic and zwitterionic surfactants may also be used. The steps involved in the development of an extraction method for microbial ATP using the firefly assay including neutralisation of the surfactant by cyclodextrins are illustrated in the examples.

EXAMPLE 1

Titration of selected extractants with cyclodextrins

A series of potential extractants was selected among various surfactants known from preliminary experiments to rapidly inactivate firefly luciferase. The extractants included dodecyl trimethyl ammonium bromide (DTAB; Sigma Chemical Co: D8638), cetyl pyridinium chloride (CPC; Sigma Chemical Co; C9002), benzalkonium chloride (BAC; ACO Läkemedel AB; 10% stock solution), benzethonium chloride (BZC; Aldrich; B470-8), N-dodecyl-N, N-dimethyl-3-ammonio-1-propanesulfonate (DDAPS; Sigma Chemical Co; D4516) and sodium dodecyl sulfate (SDS; Sigma Chemical Co; L4509). DTAB, CPC, BAC and BZC are cationic surfactants belonging to the quaternary ammonium compounds. DDAPS is a zwitterionic surfactant and SDS is an anionic surfactant. The surfactants were neutralised with α-, β- or γ-cyclodextrin (αCD, βCD or γCD; Sigma Chemical Co; C4642, C4767 or C4892) or with Tween 80 (Kebo AB, Stockholm, Sweden; 1.7267).

The following solutions were prepared:

b 1. T/E buffer; 0.1 mol/l tris(hydroxymethyl) aminomethane (E. Merck, Darmstadt, F. R. G.; 8382) containing 2 mmol/l EDTA (E. Merck, Darmstadt, F. R. G.; 8418) and adjusted to pH 7.75 with acetic acid.

2. AMR; one vial of ATP Monitoring Reagent (BioOrbit Oy, Turku, Finland) reconstituted in 5 ml distilled water.

3. ATP; one vial of ATP Standard (BioOrbit Oy, Turku, Finland) reconstituted in 10 ml distilled water.

4. Stock solutions of extractants (1% w/v of SDS or 2% w/v of all other extractants) in T/E buffer.

5. Stock solutions of neutralisers, i.e. αCD, βCD or γCD (2.5% w/v) or Tween 80 (10% w/v) in T/E buffer (βCD requires warming in hot tap water to be dissolved).

The firefly reagent (AMR) contains luciferase, D-luciferin, pyrophosphate, bovine serum albumin and magnesium ions. An essentially stable light emission (decay rate <2%/min) proportional to the ATP concentration is obtained in the concentration range $10^{-11}$–$10^{-6}$ moles/l (A. Lundin, Clinical Applications of Luminometric ATP Monitoring, Thesis from the Karolinska Institute, 1990). Measurements were done on an automatic 1251 Luminometer (BioOrbit Oy, Turku, Finland) equipped with three dispensers (one each for AMR, ATP and extractant), a potentiometric recorder and a printer. Before each run a series of up to 25 cuvettes containing 0.0, 0.1, 0.2 or 0.3 ml neutraliser (2.5% αCD, 2.5% βCD, 2.5% yCD or 10% Tween 80) and T/E buffer up to 0.9 ml was loaded into the luminometer. Using a specially designed program (can be obtained from the inventor) the luminometer performed the following steps:

1. Addition of 0.1 ml AMR with mixing.
2. Addition of 0.01 ml ATP (final concentration in cuvette $10^{-7}$ mol/l) with mixing.
3. Measurement of light emission 5s, 20s and 35s after last addition.
4. Addition of 0.01 ml extractant.
5. Reiteration of steps 3 and 4 (10 times).

Results from such titration experiments are shown in FIG. 1. The first 8 additions of DTAB gives very little effect on the light emission in the presence of 0.5% αCD. The ninth and subsequent additions give inhibition (discontinuous drop of light emission) as well as inactivation of luciferase (increased decay rate of light emission). With DTAB and Tween 80 a clear inhibition is seen already at the first addition and inactivation is seen after the third or fourth addition. The first 7 additions of BZC gives neither inhibition nor inactivation in the presence of 0.5% βCD (the slightly increased light emission will be explained below). After the eighth addition the light emission decreases. Already the first addition of BZC gives inhibition in the presence of Tween 80 although inactivation is significant only after the eighth addition.

The procedure described above allowed the measurement of the effects on the light emission after 10 additions of extractant. After each addition the decay rate of the light emission was calculated from measurements at times of 20 and 35 s assuming a first-order reaction. The rate constant and the 20 s light emission value were used to extrapolate the light emission back to the time of addition of extractant (0 s). From these extrapolated light emission values the fraction remaining light emission after each addition of extractant was calculated by dividing with the light emission before addition of extractant (35 s value). Multiplying these fraction values for each addition of extractant resulted in a series of relative light emission values affected by inhibition but not by the time dependent inactivation. Relative light emission and decay rate were finally plotted versus extractant concentration at the various types and concentrations of neutralisers (0.25, 0.50 and 0.75% αCD, βCD and yCD as well as 1, 2 and 3% Tween 80). The results are shown in FIG. 2–7. Results without neutraliser are also shown. It should, however, be considered that bovine serum albumin (0.1% w/v in cuvette) is a partial neutraliser. Extractant concentration (% in cuvette uncorrected for the slight dilution obtained by addition of extractant) is shown on the x-axis. The y-axis shows relative light emission (starting at 100%) and decay rate (starting at 0%/min).

Results with DTAB are shown in FIG. 2. With αCD and βCD the decay rate is essentially zero until a certain level of the extractant has been reached after which the decay rate increases rapidly. With yCD and Tween 80 the decay rate increases already from low DTAB levels. With αCD relative light emission remains close to 100% until the extractant concentration has reached the level resulting in inactivation and subsequently starts to decrease. With βCD the relative light emission increases slightly with the extractant concentration until the extractant concentration has reached the level resulting in inactivation and subsequently starts to decrease. With yCD and Tween 80 the relative light emission decreases with extractant concentration. Similar results were obtained with CPC, BAC and DDAPS (FIGS. 3, 4 and 6).

Results with BZC are shown in FIG. 5 (neutralisation as in FIG. 2 except that the highest concentration of the neutralisers was omitted). Very little neutralisation effect was obtained with αCD. With βCD and yCD the decay rates were essentially zero and the relative light emission close to 100% until a certain level of the extractant was reached after which the decay rate increased rapidly followed by a rapid decrease of the relative light emission. With Tween 80 the decay rate increased continuously with a continuous decrease of the relative light emission.

Results with SDS are shown in FIG. 7 (yCD omitted). With αCD the decay rates were essentially zero until a certain extractant concentration was reached. The relative light emission started to decrease somewhat before the decay rate started to increase. With βCD and Tween 80 decay rates continuously increased with extractant concentration although remaining low up to fairly high concentrations. Relative light intensities decreased even from the lowest extractant concentrations.

The curves showing the decay rate as a function of extractant concentration at 0.25, 0.50 and 0.75% cyclodextrin were similar but were displaced towards higher extractant concentrations at higher cyclodextrin concentrations. This obviously reflects a titration effect resulting from the formation of a complex between extractant and cyclodextrin. The displacement between the curves was somewhat arbitrarily measured at a decay rate of 100%/min. The displacement was expressed as moles of extractant and was divided with moles of cyclodextrin causing the displacement. If the decay rate is close to zero up to a certain level of the extractant and then increases rapidly, this should give a fairly accurate value of the molar ratio between extractant and cyclodextrin in the inclusion complex. A low association constant of the inclusion complex resulting in a fraction of the extractant being in free form or an extractant-cyclodextrin complex being luciferase inactivating in itself should give a less obvious titration effect. This would give only a poor estimate of the molar ratio in the complex. With αCD the molar ratios were: 0.90 (DTAB), 0.48 (CPC), 0.71 (BAC), 0.89 (DDAPS) and 1.07 (SDS). With βCD the molar ratios were: 0.86 (DTAB), 0.45 (CPC), 0.74 (BAC), 0.85 (BZC), 0.93 (DDAPS) and 1.25 (SDS). With yCD the molar ratio was 0.87 (BZC) and 0.89 (DDAPS). BAC is a mixture of several molecular species and the molecular weight had to be estimated from the most predominant species ($C_{12}H_{25}NC_9H_{13}Cl$. Thus results were compatible with a 1:1 stoichiometry for all detergents except CPC. The CPC molecule has an aromatic ring structure as well as a long aliphatic hydrocarbon tail. Thus two cyclodextrin molecules may be bound resulting in a molar ratio of 0.50. A 1:1 stoichiometry has been claimed for most of the extractants used in this study (cf. references above).

An important aspect of a neutraliser is its own effect on the light emission in the absence of extractant. FIG. 8 shows that the light emission was little if at all affected by Tween 80, while the cyclodextrins caused a slight inhibition at increasing concentrations. The inhibition was strongest with βCD. It seemed likely that the inhibition was due to cyclodextrins forming inclusion complexes with D-luciferin with the highest binding constant with βCD. This would explain the increased activity obtained with βCD and increasing concentrations of most extractants (DTAB, CPC, BAC and DDAPS). According to this explanation the increasing activity could be abolished by using a somewhat higher concentration of D-luciferin. This hypothesis was confirmed in the experiments shown in FIG. 9–10. A firefly reagent containing 0.25 mg/l luciferase (Enzymatix Ltd., Cambridge, U.K.), various concentrations of D-luciferin (BioThema AB, Dalarö, Sweden), 5 mmol/l magnesium acetate, 0.001 mmol/l tetrasodium pyrophosphate (Sigma Chemical Company, Missouri, U.S.A.; T6379) and 0.1% bovine serum albumin (A4503, Sigma Chemical Company, Mo., U.S.A.) was made up in T/E buffer with and without 0.75% βCD. After adding $10^{-8}$ mmol/l ATP the essential stable light emission was measured in a 1250 Luminometer (BioOrbit Oy, Turku, Finland). In preliminary experiments (not shown) the optimum D-luciferin concentration in the absence of βCD had been found to be 0.2 g/l. FIG. 9 shows that increasing the D-luciferin concentration in the absence of βCD decreased the light emission (substrate inhibition). In the presence of βCD the light emission was strongly increased going from 0.2 to 0.4 g/l, was slightly increased going from 0.4 to 0.6 g/l and was slightly decreased going from 0.6 to 0.8 g/l D-luciferin. The shift of the optimum D-luciferin level from 0.2 g/l in the absence of βCD to 0.6 g/l in the presence of 0.75% βCD is a strong indication of βCD forming an inclusion complex with D-luciferin.

Addition of a single 10 μl volume of 5% DTAB to the firefly reagents not containing βCD resulted in a rapid decay of the light emission due to inactivation of luciferase (not shown). In the presence of 0.75% (6.6 mmoles/l) βCD a slow decay of the light emission was found at the fourth addition of DTAB corresponding to 0.2% (6 mmoles/l) DTAB in the cuvette. The relative light intensities from the reagents containing various D-luciferin levels after subsequent additions of DTAB are shown in FIG. 10. Measurements were done immediately after the additions of DTAB and were not affected by time dependent inactivation of luciferase from DTAB. At the strongly suboptimal D-luciferin level (0.2 g/l or 0.7 mmoles/l) addition of DTAB increased the relative light emission. At the slightly suboptimal (0.4 g/l) D-luciferin level addition of DTAB had very little effect on the light emission. At optimum (0.6 g/l) and higher (0.8 g/l) D-luciferin addition of DTAB decreased the light emission. The most likely explanation for these effects is that DTAB has a higher affinity for βCD as compared to D-luciferin. Thus addition of DTAB releases D-luciferin from the βCD complex resulting in an increased light emission in the presence of strongly suboptimal D-luciferin levels, an essentially unchanged light emission in the presence of slightly suboptimal D-luciferin levels and a decreased light emission in the presence of optimum or higher D-luciferin levels.

Table 1 summarises the results shown in FIGS. 2–7. The table shows the lowest concentration (expressed as % in final assay mixture) of all 6 extractants that caused an inhibition ≧5% or a decay rate ≧2%/min. In the experiments extractants were added in steps of 0.02% except for SDS for which each step was 0.01%. The letter "d" after the concentration means that the decay rate was ≧2%/min. The letter "i" means that the inhibition was ≧5%. The cut-off limits for unacceptable inhibition and decay rate may seem somewhat arbitrarily defined. What they mean in practical terms is that a sample that gives a full 5% inhibition and a full 2%/min decay rate during a 2.5 minute delay between mixing of sample and reagent will give an ATP value that is 10% too low. Effects at this level may be mathematically compensated for by using a strictly controlled analytical procedure.

TABLE 1

Lowest extractant concentration resulting in an inhibition ≧5% or a decay rate ≧2%/min in the presence of various neutralisers.[1]

| Neutraliser | Conc (%) | DTAB | CPC | BAC | BZC | DDAPS | SDS |
|---|---|---|---|---|---|---|---|
| None | | 0.02 d | 0.02 d + i | 0.02 d | 0.02 d | 0.04 d | 0.01 i |
| αCD | 0.25 | 0.10 d* | 0.06 d + i* | 0.06 d* | 0.02 d | 0.10 d* | 0.02 i* |
| | 0.50 | 0.16 d + i* | 0.08 i* | 0.10 d* | 0.02 d | 0.18 d* | 0.04 i* |
| | 0.75 | 0.20 d* | 0.12 i* | 0.16 d* | n.d. | n.d. | 0.06 i* |
| βCD | 0.25 | 0.08 d | 0.02 d | 0.04 d | 0.10 d* | 0.10 d | 0.01 i |
| | 0.50 | 0.14 d | 0.04 d | 0.08 d | 0.16 d* | 0.16 d | 0.01 i |
| | 0.75 | 0.18 d | 0.08 d | 0.10 d | n.d. | n.d. | 0.01 i |
| γCD | 0.25 | 0.04 d | n.d. | n.d. | 0.08 d + i | 0.04 d | n.d. |
| | 0.50 | 0.04 d | n.d. | n.d. | 0.08 i | 0.04 i | n.d. |
| | 0.75 | 0.04 d | n.d. | n.d. | n.d. | n.d. | |
| Tween 80 | 1.00 | 0.04 d | 0.04 i | 0.04 i | 0.04 i | 0.06 i | 0.01 i |
| | 2.00 | 0.04 i | 0.04 i | 0.04 i | 0.40 i | 0.06 i | 0.01 i |
| | 3.00 | 0.04 i | 0.04 i | 0.04 i | n.d. | n.d. | 0.01 i |

[1]The letter "d" after the concentration means that the decay rate was ≧2%/min. The letter "i" means that the inhibition was ≧5%. The sign "*" after the concentration indicates best combination of detergent and cyclodextrin for which molar ratios detergent/cyclodextrin were calculated (cf. below).

In the experiments summarised in Table 1 the extractants were added to result in step-wise increases of the concentrations by 0.02% except with SDS for which each step was 0.01%. Thus subtraction of 0.02% (or 0.01% for SDS) from the concentrations in the table gives acceptable concentrations that would not give analytical interference. The results can be described as follows:

1) Without neutraliser the acceptable concentration of the extractants included in the experiment was ≦0.02% and the major problem at higher concentrations was the decay rate.

2) αCD was the best neutraliser with all the extractants except BZC for which βCD was better. The situation was improved by increasing the cyclodextrin concentration in the interval 0.25–0.75%. Except with SDS the decay rate rather than the inhibition was the limiting factor using cyclodextrins.

3) It can be calculated that the average molar ratios for acceptable detergent concentrations with αCD were: 0.88 for DTAB, 0.37 for CPC, 0.48 for BAC, 0.93 for DDAPS and 0.19 for SDS. Corresponding ratio for BZC with βCD was 0.73. For SDS the molar ratio is considerably lower than expected from the stoichiometry. It seems likely that the association constant is too low to keep all of the extractant neutralised as inclusion complex unless the ratio between SDS and αCD is kept ≦0.19.

4) With Tween 80 the acceptable concentration was generally 0.02% (0.04% for DDAPS and <0.01 for SDS) and the major problem was inhibition. The situation was not improved by increasing the Tween 80 concentration in the interval 1–3%.

It is concluded that cyclodextrins are better neutralisers for extractants of the surfactant type (cationic, anionic, zwitterionic) as compared to Tween 80 allowing higher concentrations of extractants to be used (lower dilution of extract required before assay). With most extractants αCD is the best neutraliser. However, if, as in BZC, the hydrophobic tail of the surfactant molecule is too bulky βCD (or with even bulkier tails perhaps yCD is better. With a cyclodextrin that shows a clear-cut titration curve (indicating the formation of an inclusion complex with a high association constant) the acceptable concentration of the extractant is essentially proportional to the cyclodextrin concentration. Thus the amount of cyclodextrin can be adjusted to the expected level of extractant in the final assay mixture. The stimulation of the light emission found with some detergents in the presence of βCD can be obviated by always performing the assay at optimum concentrations of D-luciferin taking into account the amount of D-luciferin released from βCD at the addition of extractant. Similar but much lower effects may possibly be found with αCD and yCD, since they also show some inhibition of the light emission (FIG. 8). The remedy would then be the same as for βCD, i.e. a somewhat higher concentration of D-luciferin.

EXAMPLE 2

Optimisation of type and concentration of extractant

The extraction of ATP from a certain type of cell is mainly influenced by type and concentration of extractant, type of cell and overall sample composition. Minor influences from number of cells, physiological conditions of cell (growth phase etc.) and variations of composition of medium should be expected. High buffering capacity will affect extraction with acids and high levels of protein or lipid will affect extraction with surfactants. Thus for any given type of cell in a given type of medium it is necessary to find optimum extraction conditions. Comparing the ATP yield obtained with several types of extractants for each type using several concentrations is the only way to find optimum extraction conditions reflecting actual intracellular ATP concentrations. From previous studies (A. Lundin, Extraction and automatic luminometric assay of ATP, ADP and AMP. In Analytical Applications of Bioluminescence and Chemiluminescence, L. Kricka, P. Stanley, G. Thorpe and T. Whitehead, Eds., pp. 545–552, Academic Press, New York, 1984) it is known that maximum ATP yields in most situations can be determined by comparing yields with 10, 5 and 2.5% trichloracetic acid (TCA). Thus a comparison of various extractants should always include TCA as a reference method. The final type and concentration of extractant should be chosen so that minor changes in the sample will not affect the ATP yield. If an extractant even at optimum concentration gives significantly less than another extractant this indicates that the yield will be variable and may be considerably reduced under even slightly modified conditions (e.g. another growth phase). The extractant concentration should be chosen to be as high as possible in the optimum concentration interval to avoid that a slightly increased concentration of sample components interfering with the extraction reduces the ATP yield in these samples.

An experiment was performed to find optimum types and concentrations of various extractants with samples containing several types of microorganisms. The extractants were cationic surfactants of the quaternary ammonium type (DTAB and BZC), a zwitterionic surfactant (DDAPS) and an anionic surfactant (SDS). TCA was included as a reference method. The microorganisms included bacteria (*Ps. aeruginosa*, *E. coli* and *B. stubilis*), a yeast (*Saccharomyces cerevisiae*) and an algae (*Chlorella vulgaris*). The bacteria were grown without shaking over-night at 30° C. in Luria broth (5 g/l NaCl, 10 g/l Tryprone and 5 g/l Yeast extract). The yeast was grown over-night without shaking at 37° C. in Luria broth. The Chlorella was obtained as a ready-made culture from a type culture collection of algae and protozoa (Freshwater Biological Association, The Ferry House, Ambleside, Cumbria LA22 OLP, U.K.). All cultures except Chlorella were 10-fold diluted in Analar water. Two-fold dilutions of extractants were prepared to contain: 10, 5, 2.5, 1.25, 0.625, 0.3125, 0.15625, 0.078125, 0.0390625, 0.01953125 and 0.009765625% extractant in 5 mmol/l EDTA. Equal volumes (0.1 ml) of extractant and diluted samples were mixed. After 1 and 30 minutes 50 µl aliquots of the resulting extracts were transferred to two series of parallel cuvettes containing 0.85 ml T/E buffer containing 2% Tween 80. Tween 80 neutralises the enzyme inhibiting effect of the extractant. Extracted ATP is, however, expected to be essentially stable after dilution in the presence of EDTA complexing divalent metal ions required for enzyme reactions involving ATP. At high concentrations of the extractant the extraction is completed within seconds but at low concentrations the extraction takes considerably longer times and gives poor yields. Comparing results from the first and second series at high concentrations of the extractant provides an estimate of the stability of ATP in the extracts. In this experiment Tween 80 rather than cyclodextrins was used, since the assay could be performed with highly diluted samples using an automatic 1251 Luminometer with addition of ATP standard in each individual assay. Cuvettes were loaded into the luminometer and the following assay procedure was automatically performed:

1) Temperature equilibration to 25° C. (10 min).
2) Addition of 0.1 ml AMR.
3) Measurement of the light emission, $I_{smp}$, after a 20 s delay.
4) Addition of 0.01 ml ATP Standard.
5) Measurement of light emission, $I_{smp+std}$, after a 20 s delay.

The delays were included to ascertain that a stable light emission was obtained. The ATP concentration in the cuvette, $C_{smp}$, was calculated by the formula:

$$C_{smp}=C_{std}*I_{smp}/(I_{smp+std}-I_{smp})$$

Appropriate corrections for dilutions and blanks (no extractant giving extracellular ATP only) were performed to assure that only intracellular ATP was measured. Results are shown in FIG. 11–15.

With *Ps. aeruginosa* (FIG. 11) and *E. Coli* (FIG. 12) similar ATP yields were obtained with optimum concentrations of DTAB, BZC and TCA. Neither the zwitterionic surfactant (DDAPS) nor the anionic surfactant (SDS) could be used. With *B. subtilis* (FIG. 13), *Saccharomyces cerevisiae* (FIG. 14) and *Chlorella vulgaris* (FIG. 15) similar yields were obtained with optimum concentrations of all five extractants. A decision on preferred extractant for any one of the microorganisms can not be made from the data in FIGS. 11–15. Such a decision would require more elaborate experiments including e.g. studies on cells in different phases of growth. Furthermore if cells would be suspended in other media in actual samples it would be necessary to perform extractions in such media. If actual samples would contain several microbial strains it would be necessary to study all these strains. The data in FIGS. 11–15 can, however, be used to select extractants and for each extractant a concentration interval to be used in further experiments. Such a selection and some preliminary experiments are shown for a particular application in Example 3.

EXAMPLE 3

Use of cyclodextrin for neutralising extractants in assays of microbial ATP

The firefly assay of ATP can be used for biomass estimation in process water. Microorganisms in process water would include various bacterial, yeast and algal strains. In model experiments overnight cultures of *Proteus vulgaris, Bacillus subtilis, Aeromonas hydrophila, Pseudomonas fluorescens, Pseudomonas aeruginosa* and *Saccharomyces cerevisiae* in both Luria broth were tenfold diluted in Analar water. The organic material from the broth may to some extent interfere with extraction using surfactants. Process water may also contain some organic material but most likely at a lower level than a tenfold diluted broth. Thus it seems likely that an extraction procedure working in the model experiment would also work in actual samples. Experiments were also performed using undiluted algal cultures (*Euglena gracilis, Chlorella vulgaris* and *Anabaena cylindrica* obtained from the Freshwater Biological Association) and actual process water samples.

The three extractants that according to the data in Example 2 could be used for all types of microbial cells (bacterial, yeast and algal) were DTAB, BZC and TCA. For each of the extractants, 10, 5 and 2.5% solutions were prepared in Analar water containing 5 mmol/l EDTA. Samples (50 μl) were added to cuvettes containing an equal volume of the extractant solutions and 0.8 ml T/E buffer was subsequently added. For extracts containing DTAB the buffer also contained 5 times as much αCD on a weight basis and for extracts containing BZC the buffer contained 4 times as much βCD. This resulted in molar ratios of 0.63 (DTAB/αCD) and 0.61 (BZC/βCD), i.e. well below the highest acceptable ratios calculated in Example 1 (0.88 and 0.73, respectively). Assays of ATP were automatically performed as in Example 2 using a 1251 Luminometer. No inactivation of luciferase by the quaternary ammonium compounds resulting in a decay of the light emission during the measurement was obtained. This was an important confirmation that the principles behind the present invention really work in practical assays of microbial ATP.

FIGS. 16–18 show typical results from model experiments with the 9 organisms described above (*Proteus vulgaris, Bacillus subtilis, Aeromonas hydrophila, Pseudomonas fluorescens, Pseudomonas aeruginosa, Saccharomyces cerevisiae, Euglena gracilis, Chlorella vulgaris* and *Anabaena cylindrical*). The two lowest TCA concentrations (working strength 1.25 and 2.5%) were inadequate with at least 4 organisms (*Bacillus subtilis, Pseudomonas aeruginosa, Saccharomyces cerevisiae* and *Chlorella vulgaris*). The highest TCA concentration (working strength 5%) gave maximum or close to maximum ATP yields in 6 organisms (all except *Bacillus subtilis, Aeromonas hydrophila* and *Chlorella vulgaris*). However, this concentration results in a serious inhibition of the light emission, which gives a lower sensitivity and makes it necessary to use internal ATP standard in every assay. Extraction with the quaternary ammonium compounds (DTAB and BZC) were little influenced by the concentration of the extractant in the interval studied. A twofold excess over optimum concentration would be preferred as a safety margin. Thus based on the experimental evidence the preferred concentration would have to be 2.5% working strength although a lower concentration might well work just as good. BZC gave maximum or close to maximum ATP yields in 4 organisms (*Aeromonas hydrophila, Pseudomonas aeruginosa* and *Saccharomyces cerevisiae*). DTAB gave maximum or close to maximum ATP yields 7 organisms (all except *Pseudomonas fluroescens* and *Anabaena cylindrica*).

The final decision on extraction method has to be based on experiments with actual samples from each application and selected to be as typical as possible. Results from such experiments with three process water samples are shown in FIG. 19. In all three samples the best results were obtained with DTAB. A similar experiment was performed with three other process water samples (0.05 ml) extracted with an equal volume of extractant solution (0.01–3.5% DTAB). The extractant was neutralised by including αCD in the assay buffer (0.85 ml) to give a final concentration of 0.875% in the assay mixture (i.e. 5 times the highest final DTAB concentration). The assay was performed by adding 0.05 ml of a firefly reagent containing 0.05 g/l luciferase (Enzymatix Ltd., Cambridge, U.K.), 4 g/l D-luciferin (BioThema AB, Dalarö, Sweden), 100 mmol/l magnesium acetate, 0.02 mmol/l tetrasodium pyrophosphate (Sigma Chemical Company, Mo., U.S.A.; T6379) and 2% bovine serum albumin (A4503, Sigma Chemical Company, Mo., U.S.A.). Every assay was calibrated by addition of $10^{-8}$ moles/l ATP standard (final concentration in 1 ml assay mixture). Measurements of light emission before and after addition of ATP standard were done using a 1251 Luminometer (BioOrbit Oy, Turku, Finland). Results from duplicate measurements (FIG. 20) indicate that 1.25% DTAB in the extract (corresponding to equal volumes of sample and 2.5% DTAB) should give a 100% ATP yield with a safety margin. For a routine application this conclusion would have to be confirmed in many more samples.

EXAMPLE 4

Use of Cyclodextrin for Neutralising Extractants in DNA Modification or Amplification Reactions In this experiment, the use of cyclodextrins was investigated for detergent neutralisation after cell lysis. HeLa cells ($10^7$) in 0.5 ml PBS (Sigma) were lysed by the addition of 1 ml of Cell Lysis Buffer (100 mM Tris, pH 8; 1 mM EDTA; 1% SDS; 0.4 mg/ml RNase A; 40 U/ml RNase T1). The lysate was incubated at 55° C. for 15 min prior to the addition of 0.5 ml of proteinase K (Boehringer; 600 μg/ml). Digestion was continued at 55° C. for 45 mins. The lysate was aliquoted (200 μl) into fresh tubes and αCD (Fluka; 10% w/v in $H_2O$) added to the lysates in the following amounts: 10 μl, 20 μl, 50 μl, 100 μl and 200 μl. Samples were mixed by gentle agitation prior to analysis of functional activity of the DNA by PCR.

The PCR reaction (50 μl reaction volume) was set up by the addition of the following: 10 μl 5×PCR buffer (50 mM Tris pH 8.5; 250 mM KCl, 7.5 mM $MgCl_2$, 1 mM dATP, 1 mM dGTP, 1 mM dCTP, 1 mM dTTP), 2 µl of CF locus primers (50 µM of each); 1 µl DNA (αCD-treated lysates or control DNA); 37 µl sterile $H_2O$; 2 µl Taq polymerase (Amersham).

| The reaction profile was as follows: | | |
| --- | --- | --- |
| 93° C. | 3 min | |
| 55° C. | 1 min | 30 cycles |
| 72° C. | 2 min | " |
| 93° C. | 30 sec | " |
| 55° C. | 1 min | " |
| 72° C. | 5 min | |

On completion of the PCR reaction, samples (20 µl) were analysed by agarose gel electrophoresis (1% agarose in TBE buffer; J. Sambrook, E. F. Fritsch and T. Maniatis, Molecular Cloning—A Laboratory Manual, second edition, Cold Spring Harbor Laboratory Press, 1989). Maximal amplification was achieved in lysates where either 50 µl or 100 µl of αCD had been added, with amplification also at 200 µl added. No amplification was generated in either the control (lysate with no αCD added) or in lysates where 10 and 20 µl of αCD had been added.

To evaluate if the samples which were amplifiable were also digestible with restriction enzymes, the following experiment was performed. Lysates which had been treated with 50 µl and 100 µl of αCD were digested with HindIII, EcoRI and MspI (Amersham) as follows: DNA (18 µl), buffer (2 µl, as supplied by manufacturer) and enzyme (approximately 5 U/µg) were mixed and samples digested for 1 hour at 37° C. Samples were analysed by agarose gel electrophoresis, as described.

The banding patterns of the αCD treated samples after restriction digestion, were examined. Only the sample with 100 µl αCD added was digestible with all three enzymes, indicating that these are the optimal neutralisation conditions for both PCR and restriction analysis of DNA in these HeLa lysates.

The PCR and restriction digest experiments indicate that αCD is effective for SDS neutralisation in crude cell lysates, and that DNA present in these lysates is functionally active.

EXAMPLE 5

Figure 1:
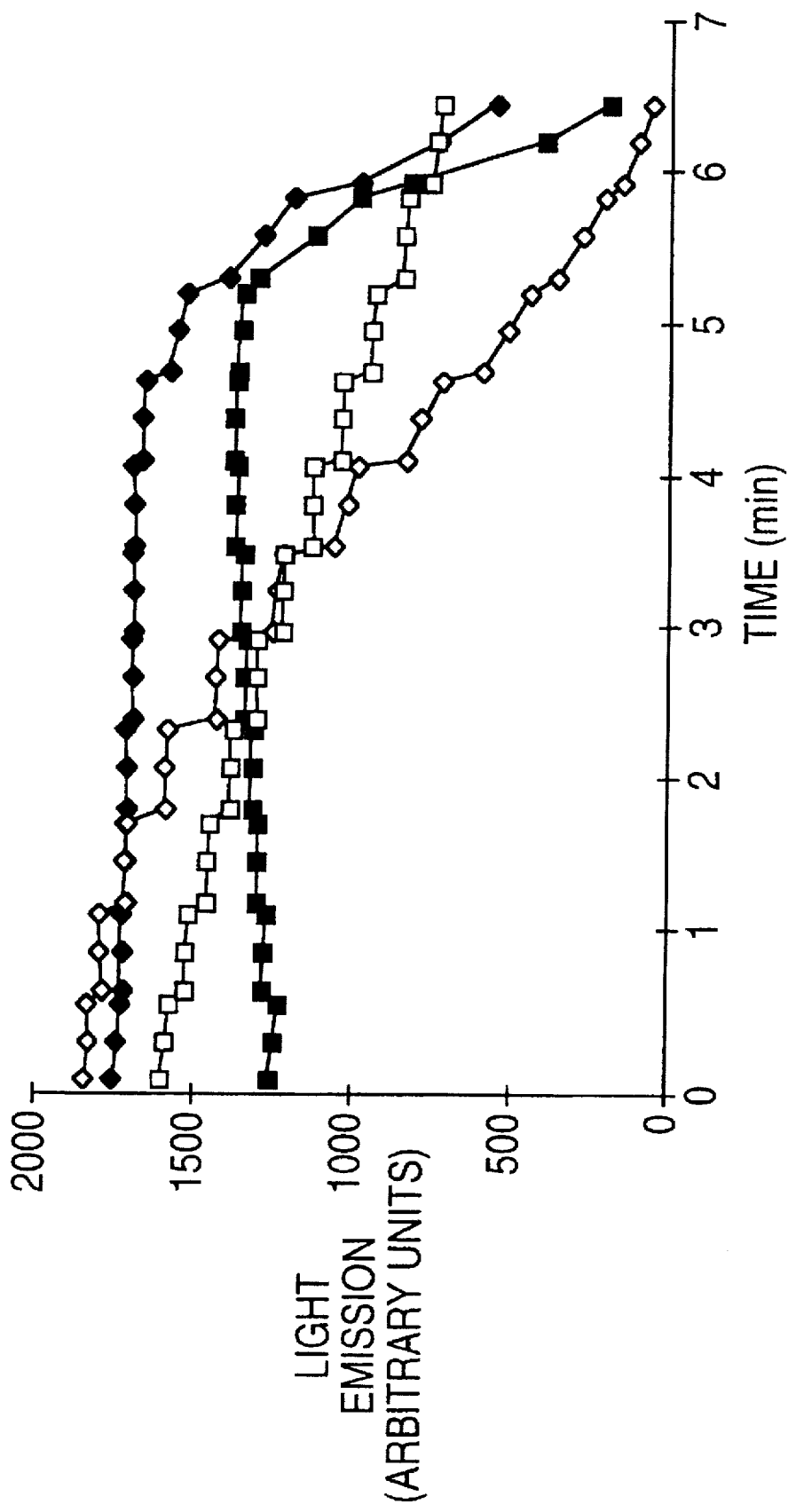
FIG. 1: Titration of neutralisers with extractants. Measurements were performed as described in the text. After each third point on the curves 10 µl of extractant was added to an approximately 1 ml reaction mixture containing the neutraliser and the firefly reagent. The figure show titrations with 2% DTAB of 0.5% αCD (♦) and of 2% Tween 80 (◊) and titrations with 2% BZC of 0.5% βCD (■) and of 2% Tween 80 (□).
Figure 2A:
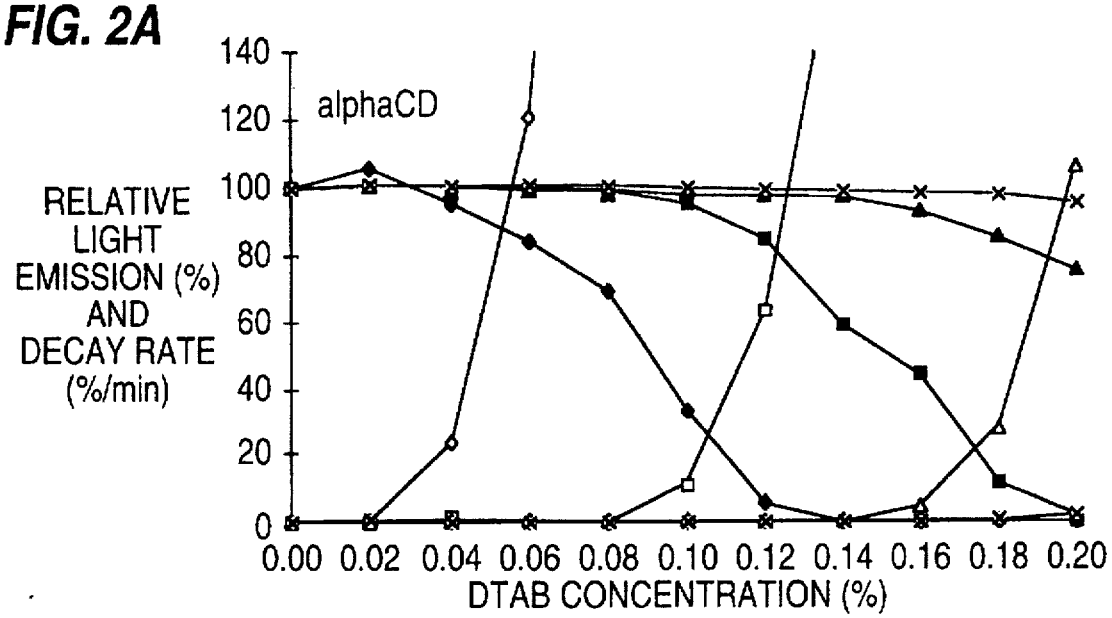
FIGS. 2A to D: Effects of DTAB on decay rate and relative light emission in presence of various neutralisers. Type of neutraliser is indicated in figure. Decay rates (%/min) are shown by the symbols: ◊(no neutraliser), □(0.25% cyclodextrin or 1% Tween 80), △(0.50% cyclodextrin or 2% Tween 80) and *(0.75% cyclodextrin or 3% Tween 80). Relative light emissions (% of value before first addition of extractant) are shown by the symbols ♦(no neutraliser), ■(0.25% cyclodextrin or 1% Tween 80), ▲(0.50% cyclodextrin or 2% Tween 80) and x (0.75% cyclodextrin or 3% Tween 80).
Figure 2B:
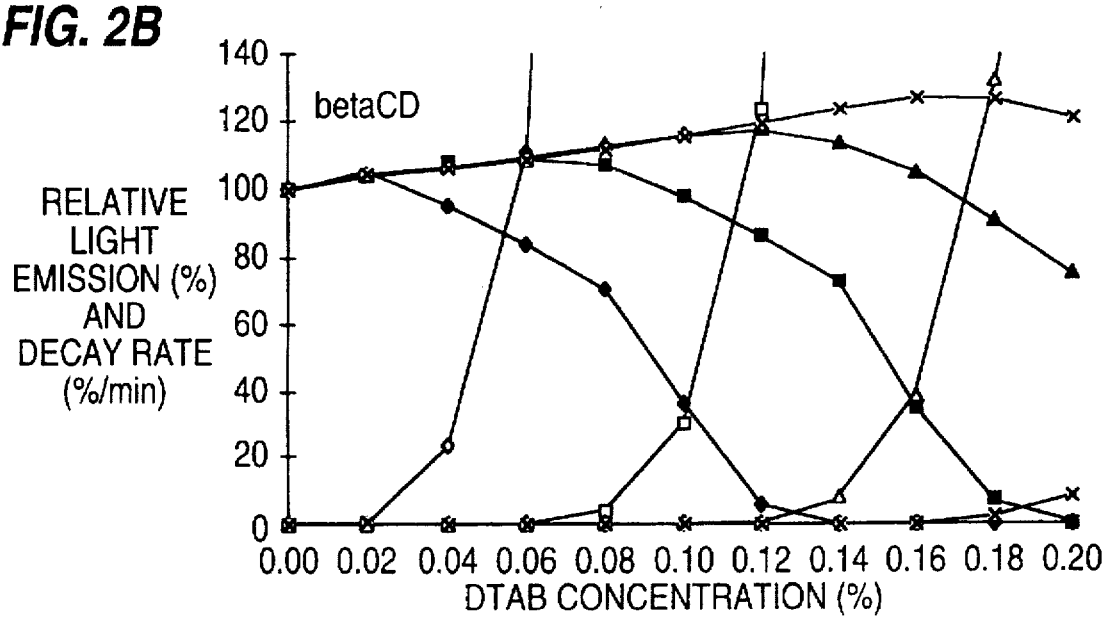
Figure 2C:
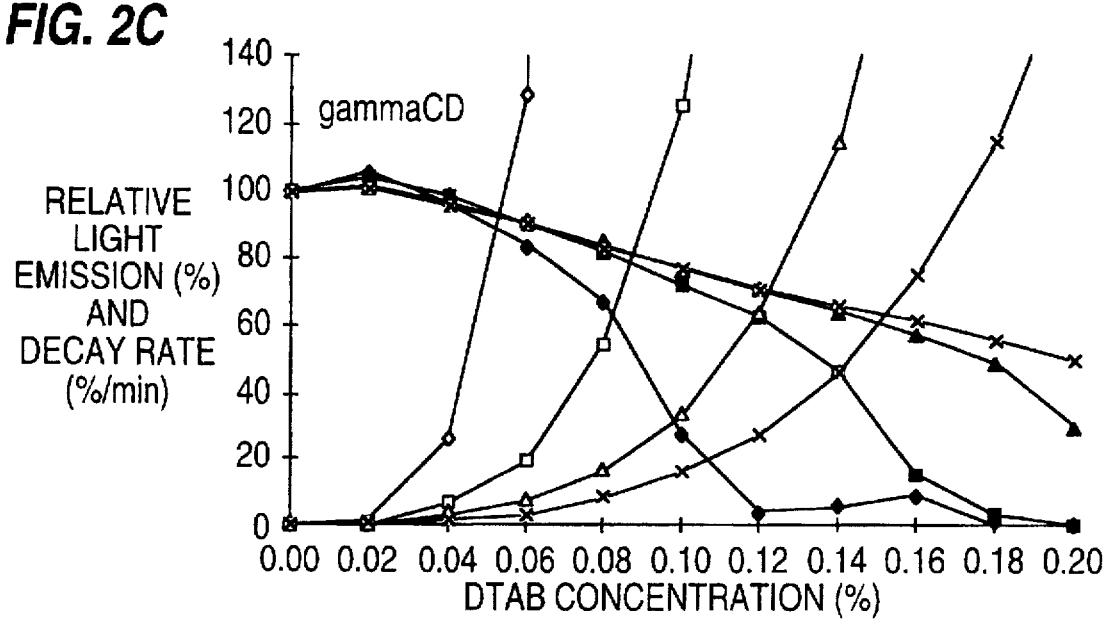
Figure 2D:
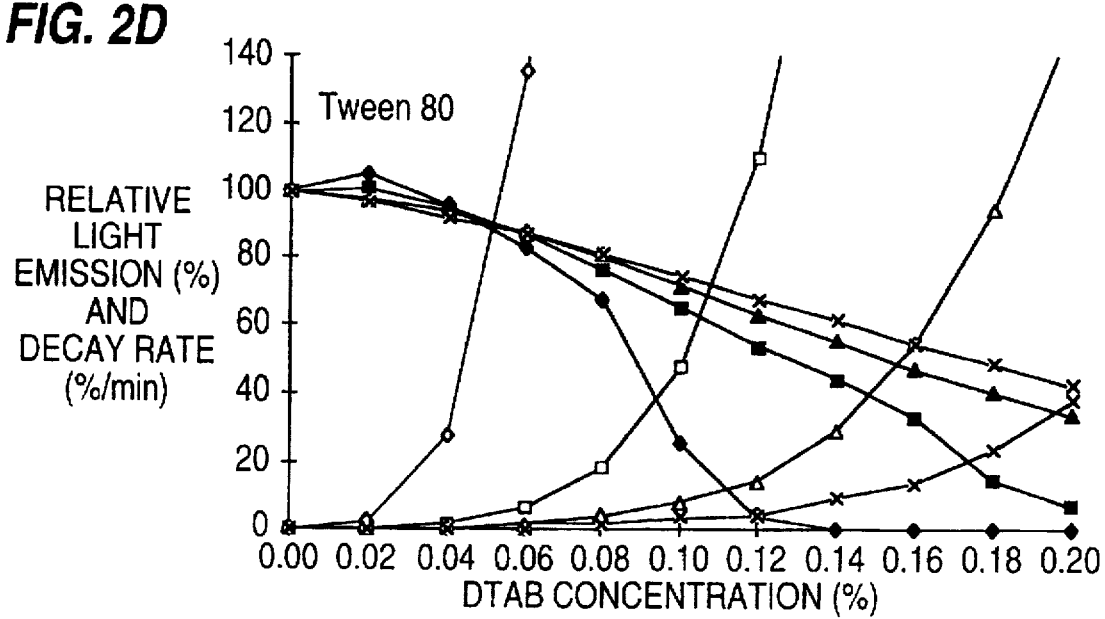
Figure 3A:
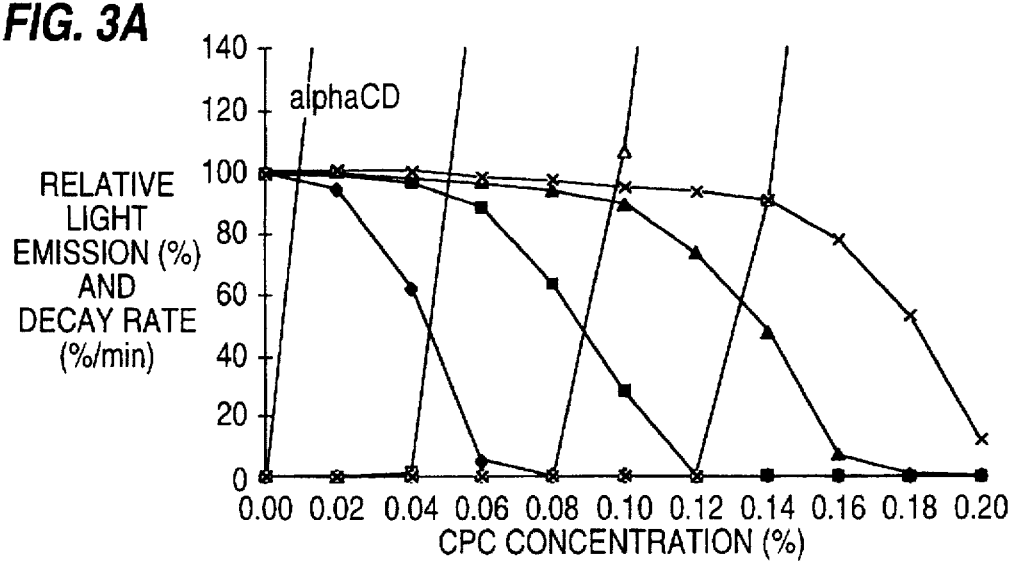
FIGS. 3A to C: Effects of CPC on decay rate and relative light emission in presence of various neutralisers. Concentrations of neutralisers and symbols as in FIG. 2 (yCD omitted).
Figure 3B:
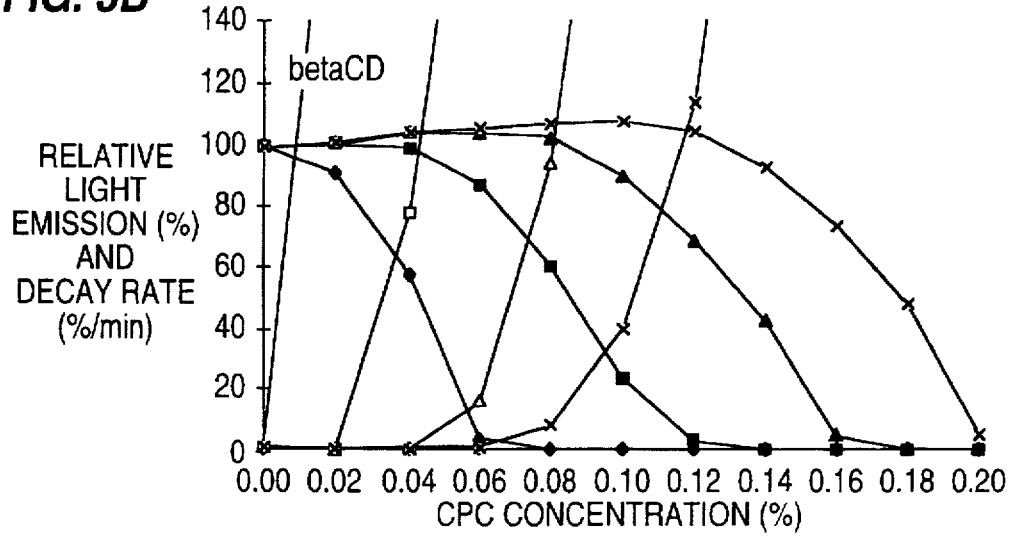
Figure 3C:
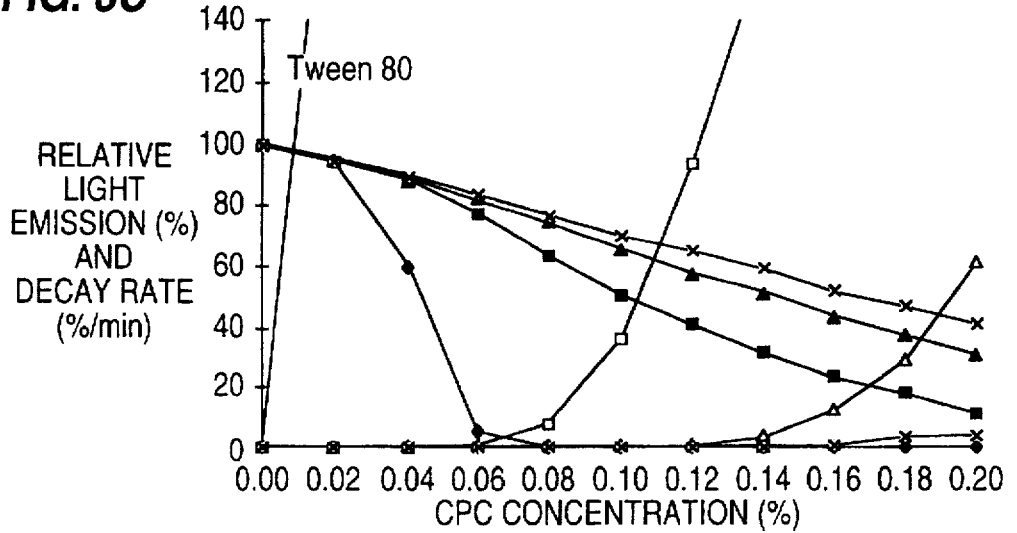
Figure 4A:
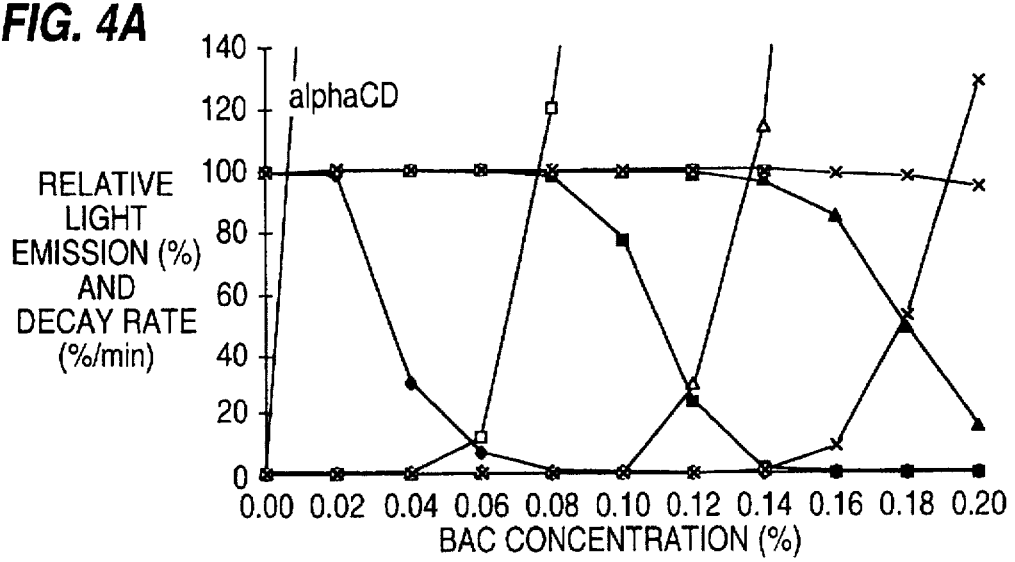
FIGS. 4A to C: Effects of BAC on decay rate and relative light emission in presence of various neutralisers. Concentrations of neutralisers and symbols as in FIG. 2 (yCD omitted).
Figure 4B:
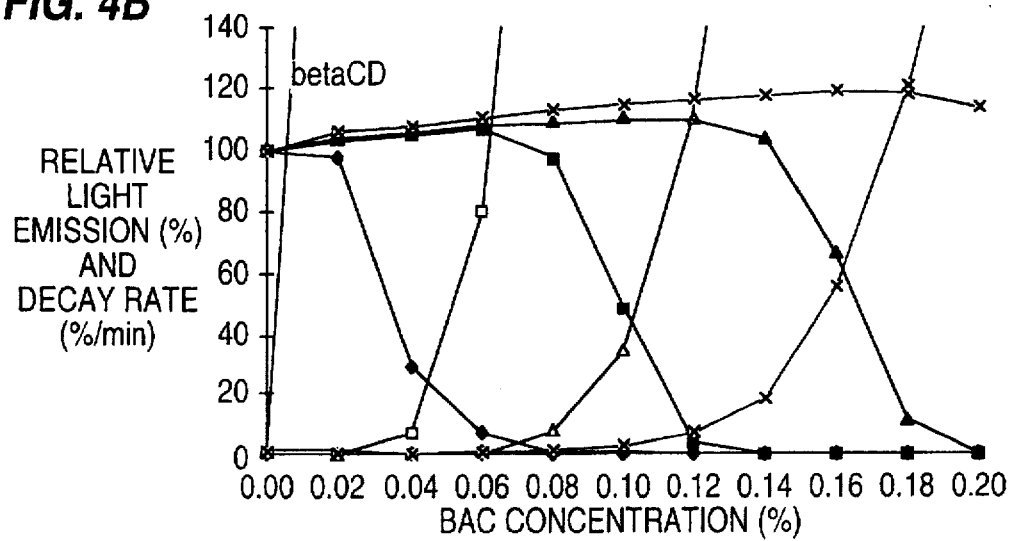
Figure 4C:
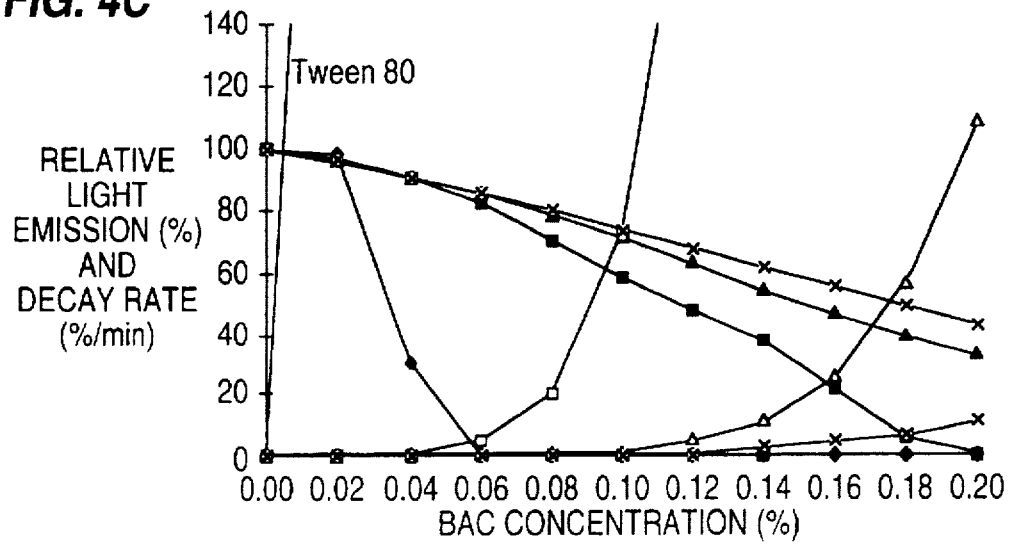
Figure 5A:
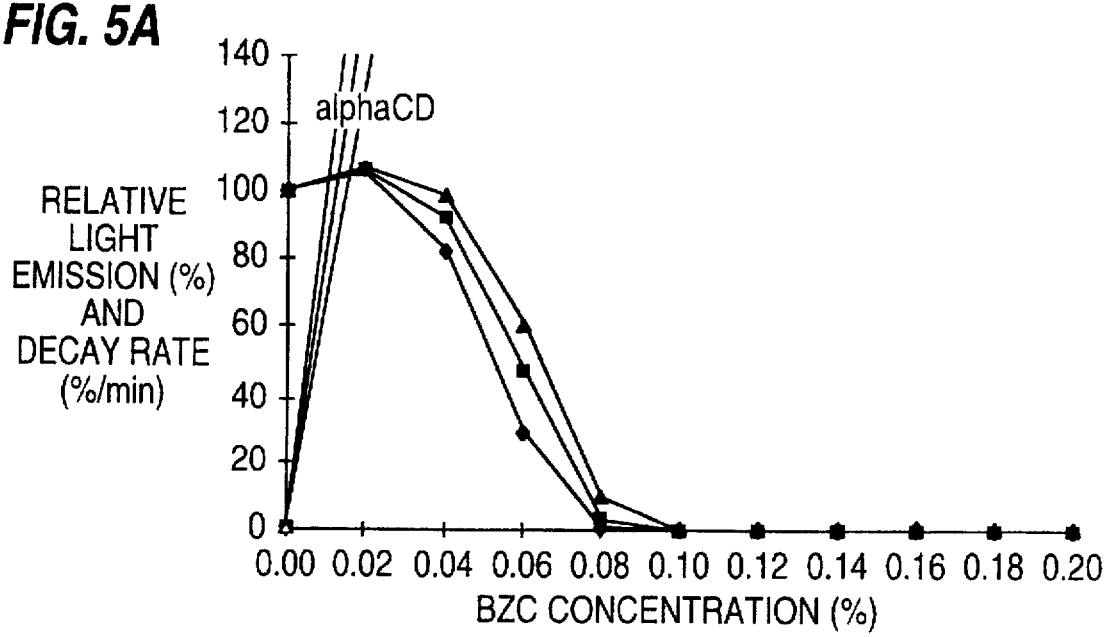
FIGS. 5A to D: Effects of BZC on decay rate and relative light emission in presence of various neutralisers. Concentrations of neutralisers and symbols as in FIGS. 2A to D (highest concentration of neutralisers omitted).
Figure 5B:
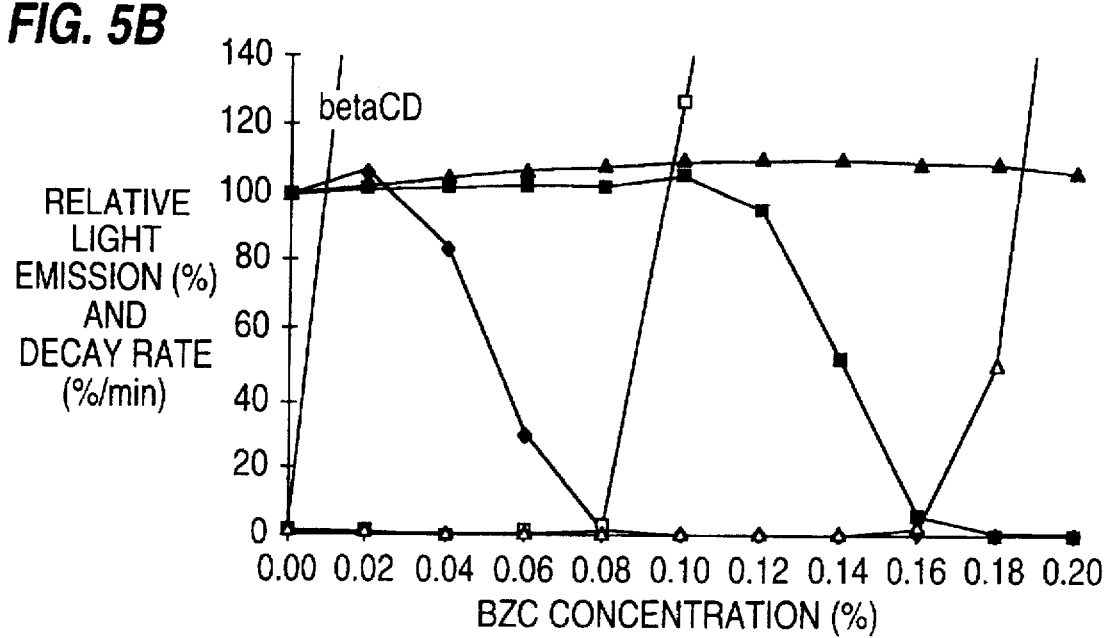
Figure 5C:
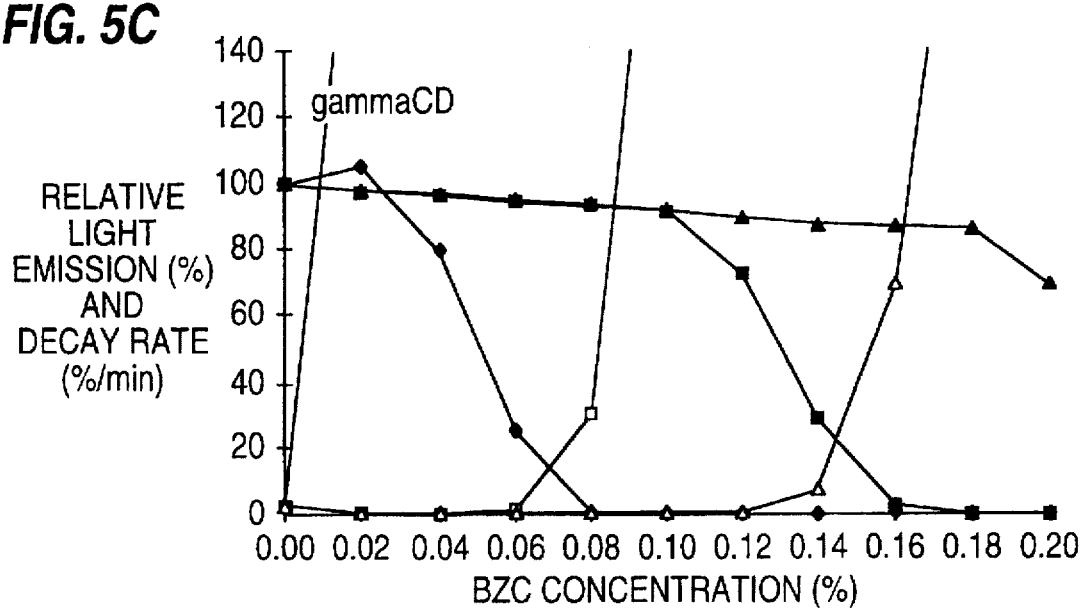
Figure 5D:
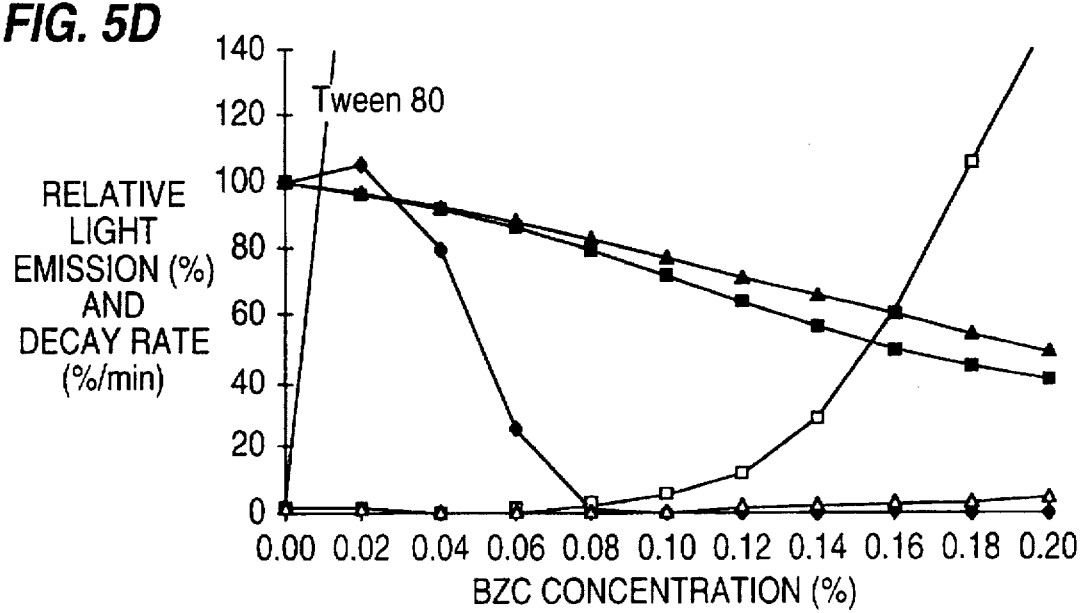
Figure 6A:
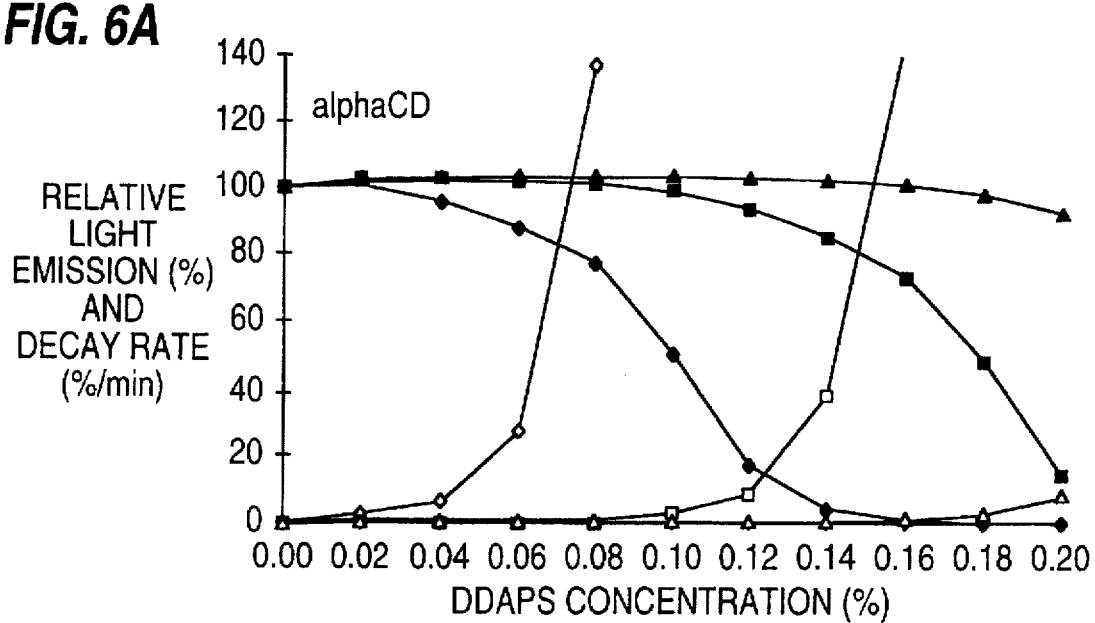
FIGS. 6A to D: Effects of DDAPS on decay rate and relative light emission in presence of various neutralisers. Concentrations of neutralisers and symbols as in FIG. 2 (highest concentration of neutralisers omitted).
Figure 6B:
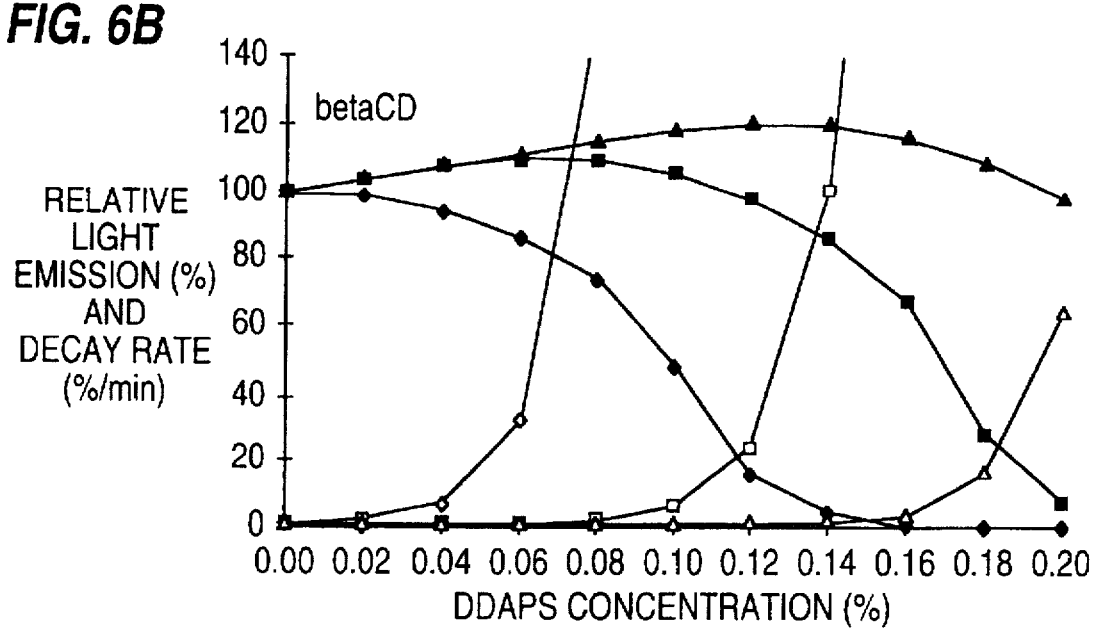
Figure 6C:
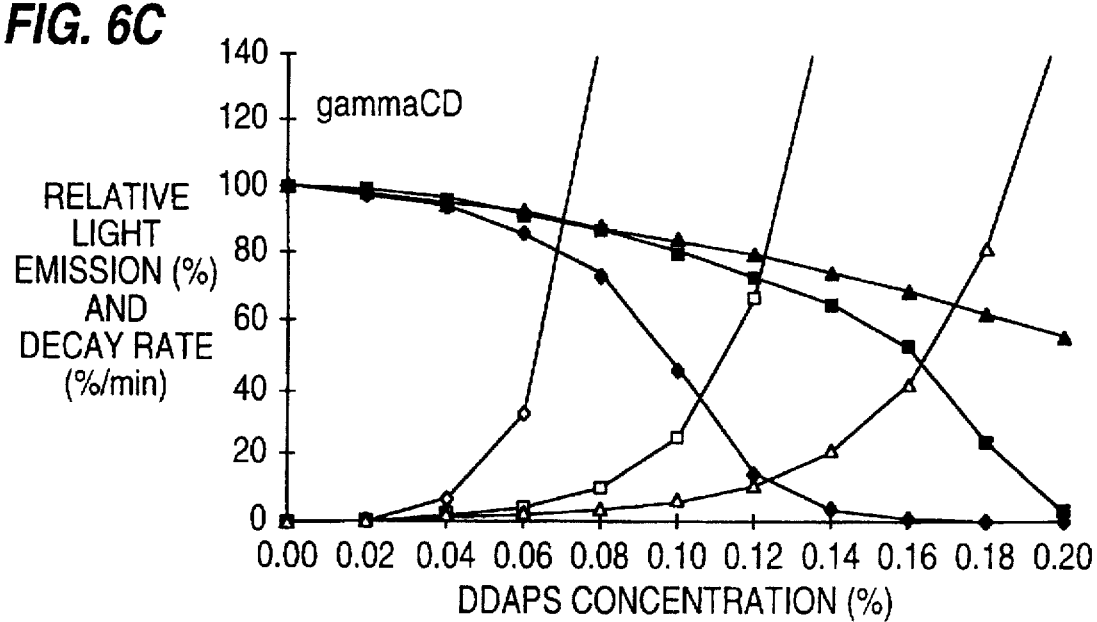
Figure 6D:
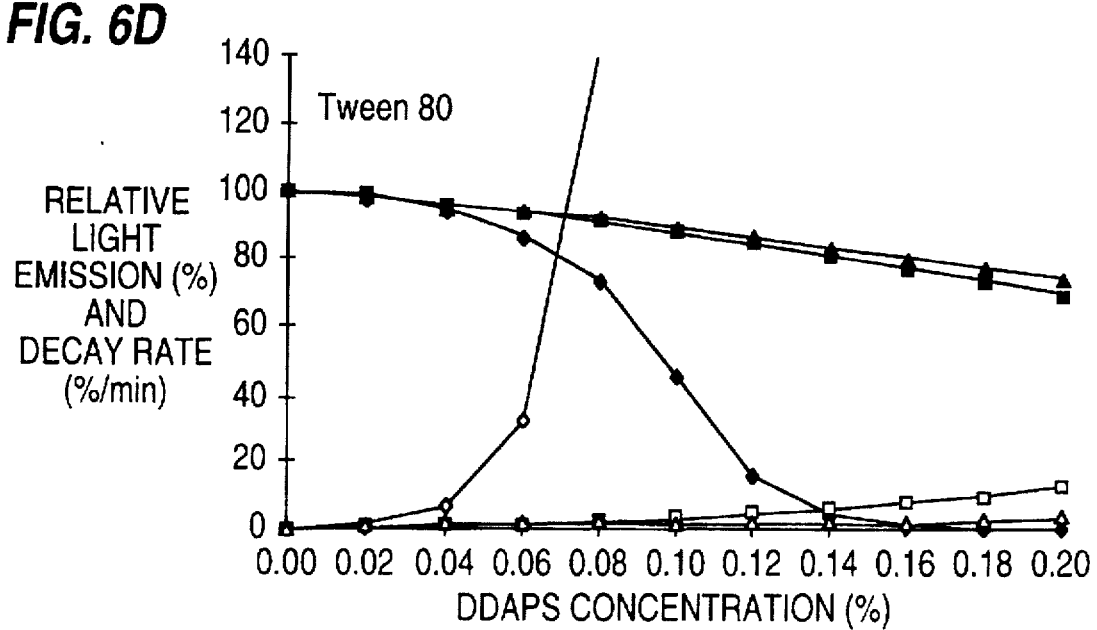
Figure 7A:
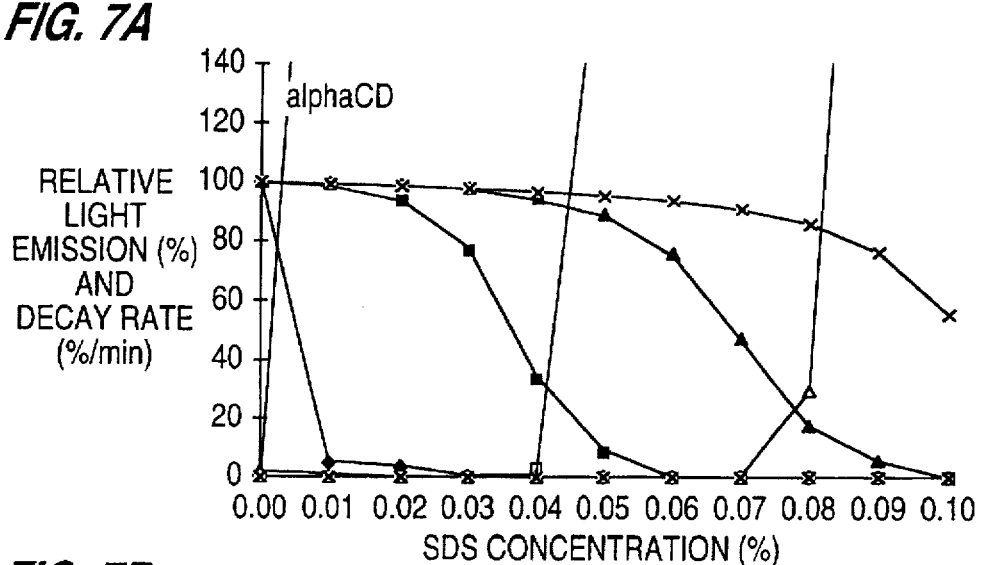
FIGS. 7A to C: Effects of SDS on decay rate and relative light emission in presence of various neutralisers. Concentrations of neutralisers and symbols as in FIG. 2 (yCD omitted).
Figure 7B:
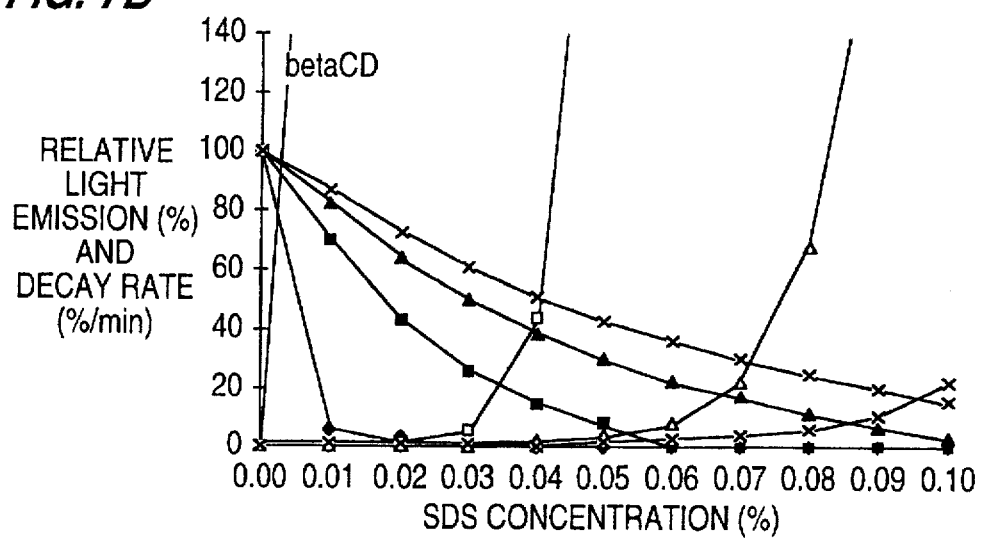
Figure 7C:
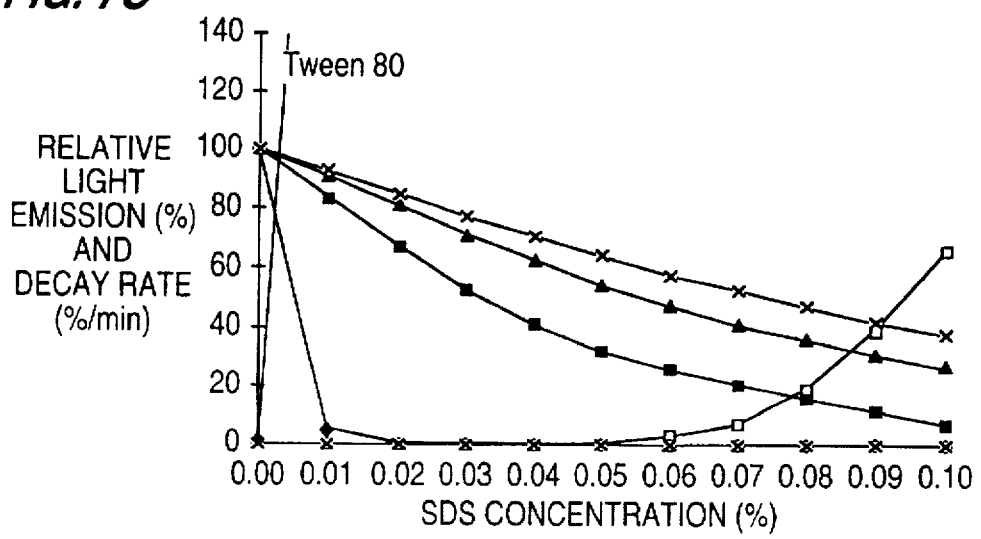
Figure 8:
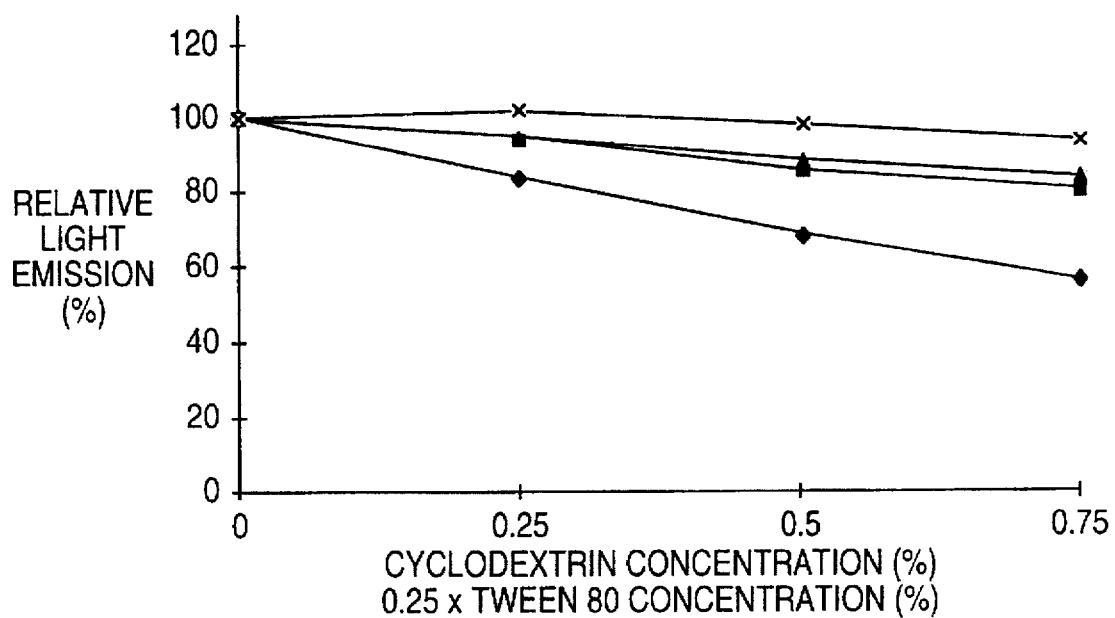
FIG. 8: Effect on relative light emission from neutralisers. Concentrations of neutralisers were: 0.25, 0.50 and 0.75% cyclodextrin (■, αCD; ♦, βCD; ▲, yCD) or 1, 2 and 3% Tween 570 (x).
Figure 9:
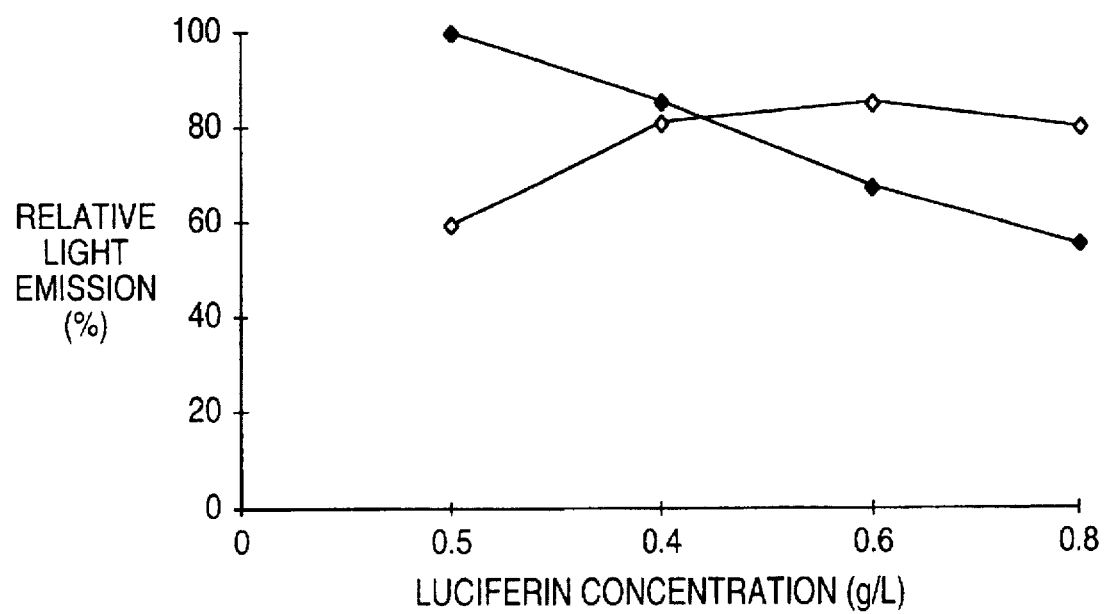
FIG. 9: Effect of luciferin concentration on relative light emission from firefly reagents in the presence of (◊) and absence (♦) of 0.75% βCD. Light emission with 0.2 g/l luciferin in the absence of βCD is set to 100%.
Figure 10:
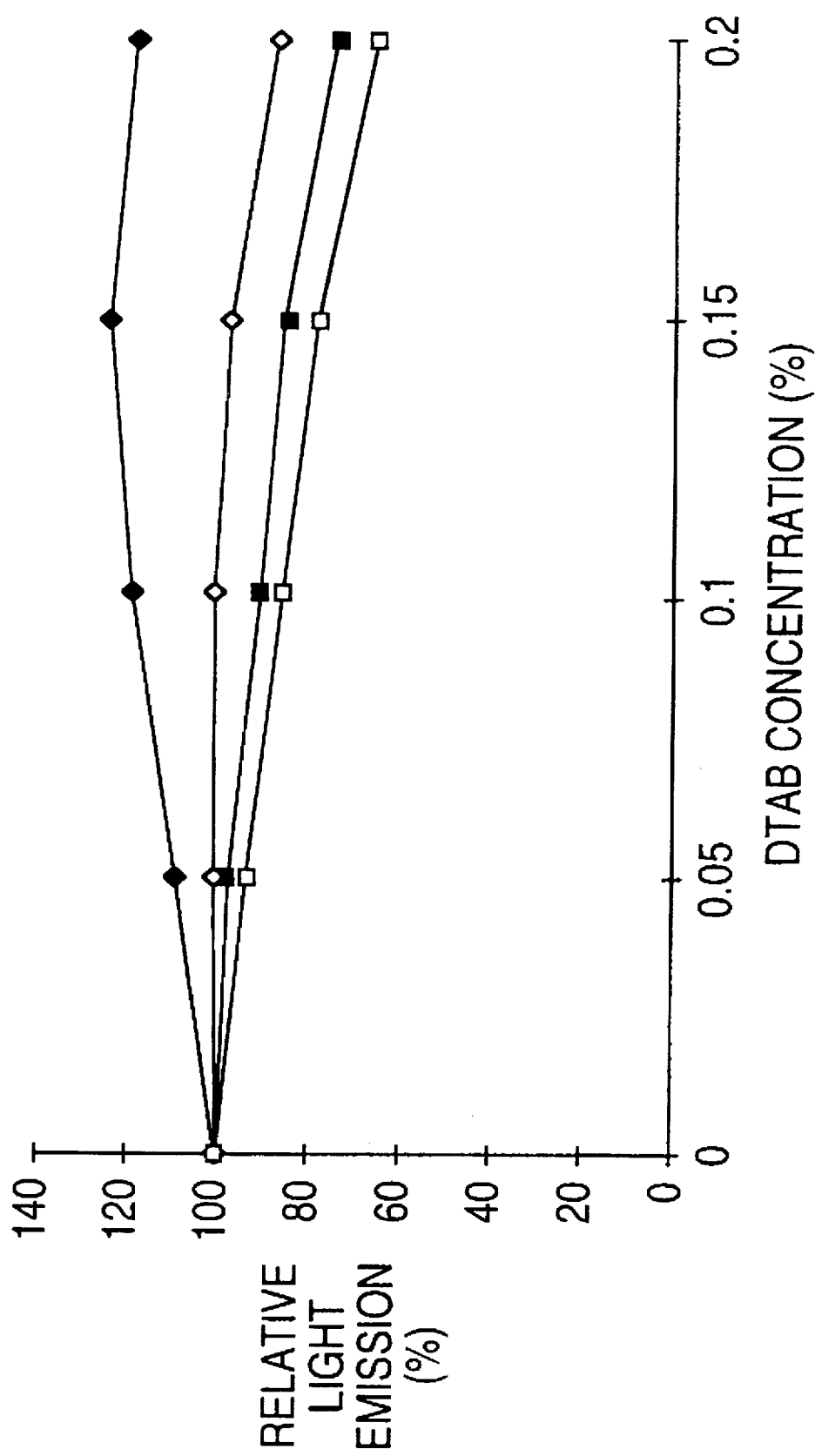
FIG. 10: Effect of DTAB on relative light emission of firefly reagents containing 0.75% βCD and various concentrations of D-luciferin (♦, 0.2 g/l; ◊, 0.4 g/l; ■, 0.6 g/l; □, 0.8 g/l). Light emission before adding DTAB to the various reagents is set to 100%.
Figure 11:
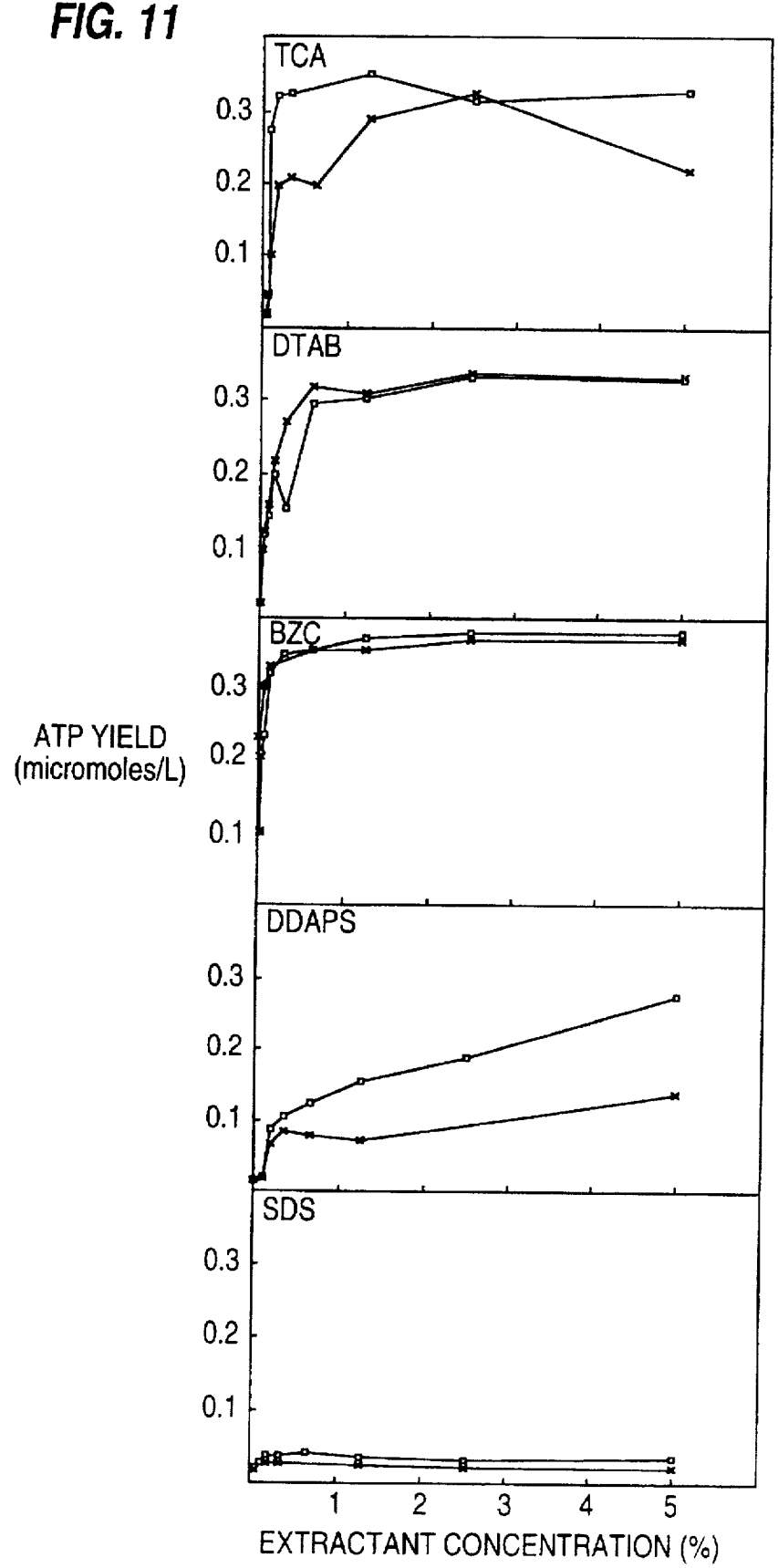
FIG. 11: Effect of extractant concentration on ATP yield in an over-night culture of Ps. auruginosa diluted 10-fold in water. Extraction times: 1 min (x) and 30 min (□).
Figure 12:
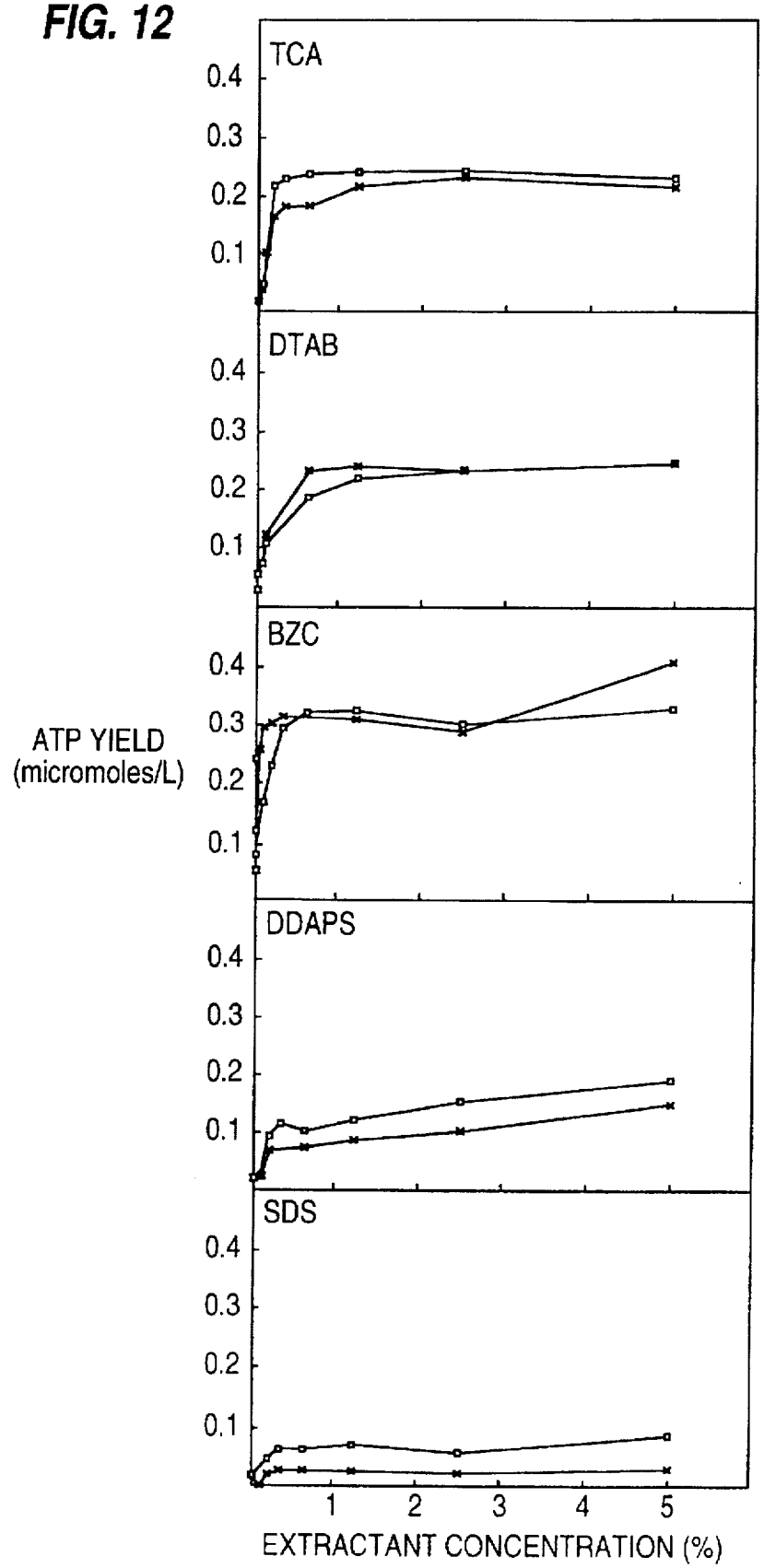
FIG. 12: Effect of extractant concentration on ATP yield in an over-night culture of E. coli diluted 10-fold in water. Extraction times: 1 min (x) and 30 min (□).
Figure 13:
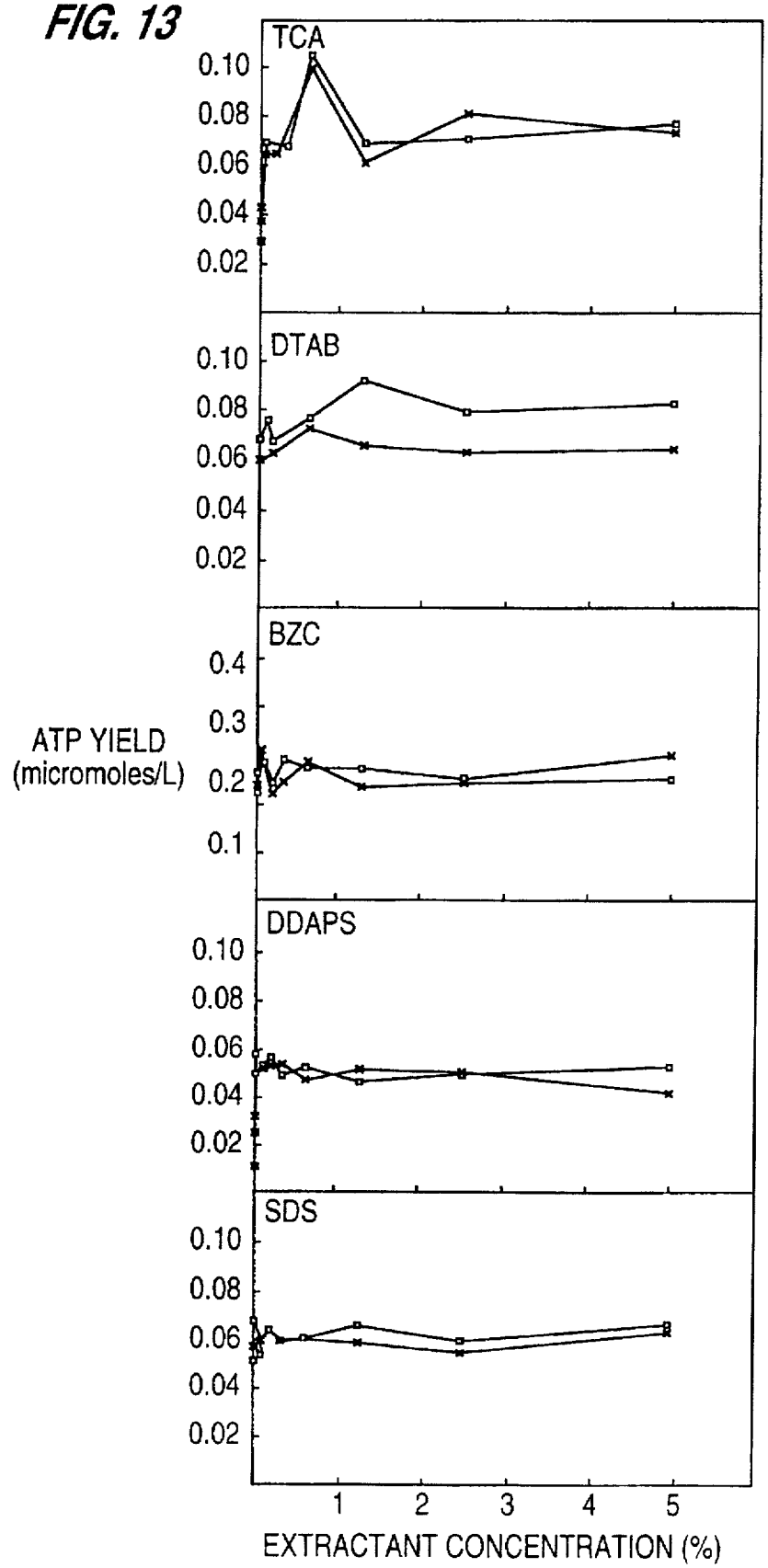
FIG. 13: Effect of extractant concentration on ATP yield in an over-night culture of B. subtilis diluted 10-fold in water. Extraction times: 1 min (x) and 30 min (□).
Figure 14:
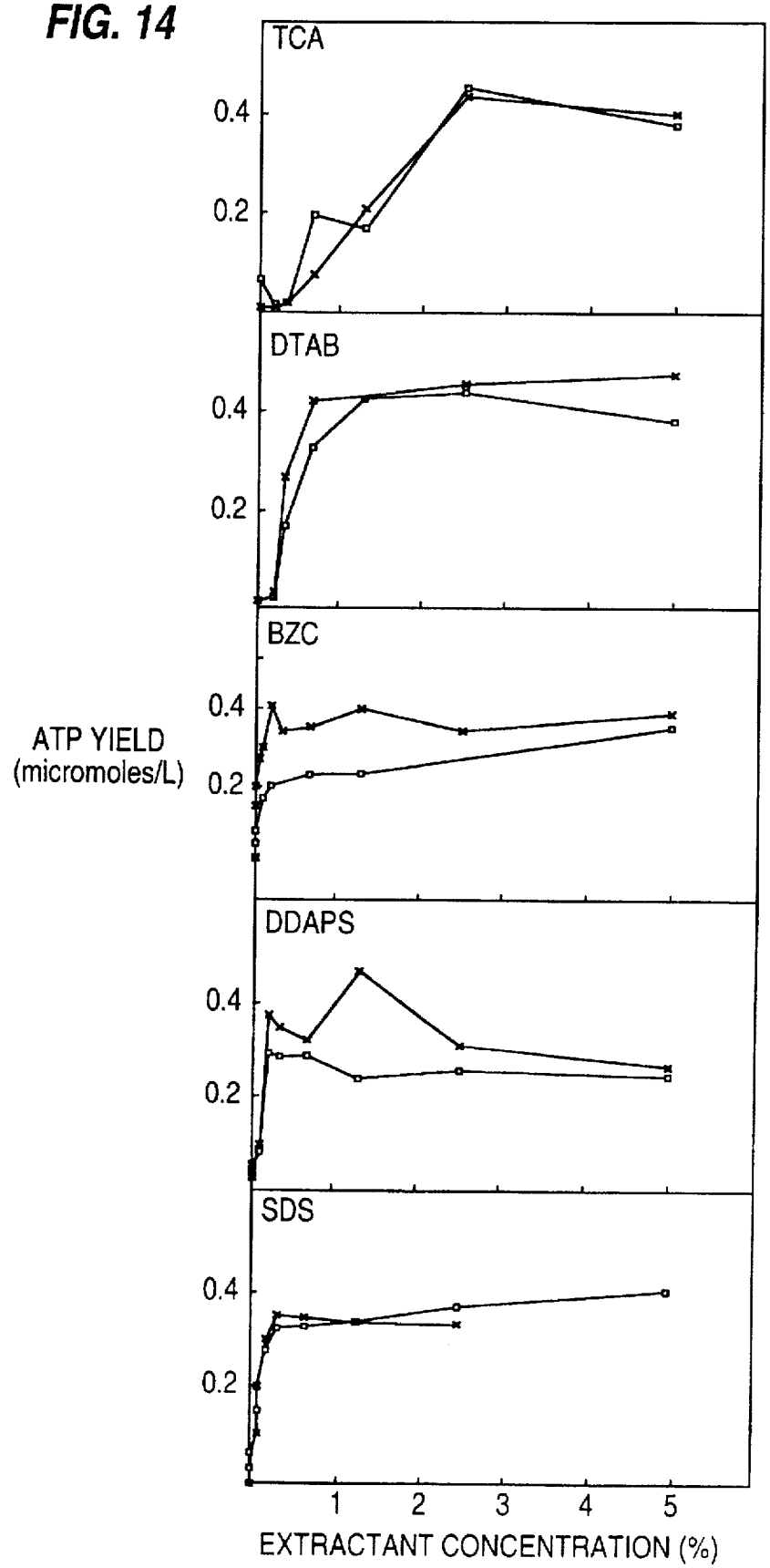
FIG. 14: Effect of extractant concentration on ATP yield in an over-night culture of Saccharomyces cerevisiae diluted 10-fold in water. Extraction times: 1 min (x) and 30 min (□).
Figure 15:
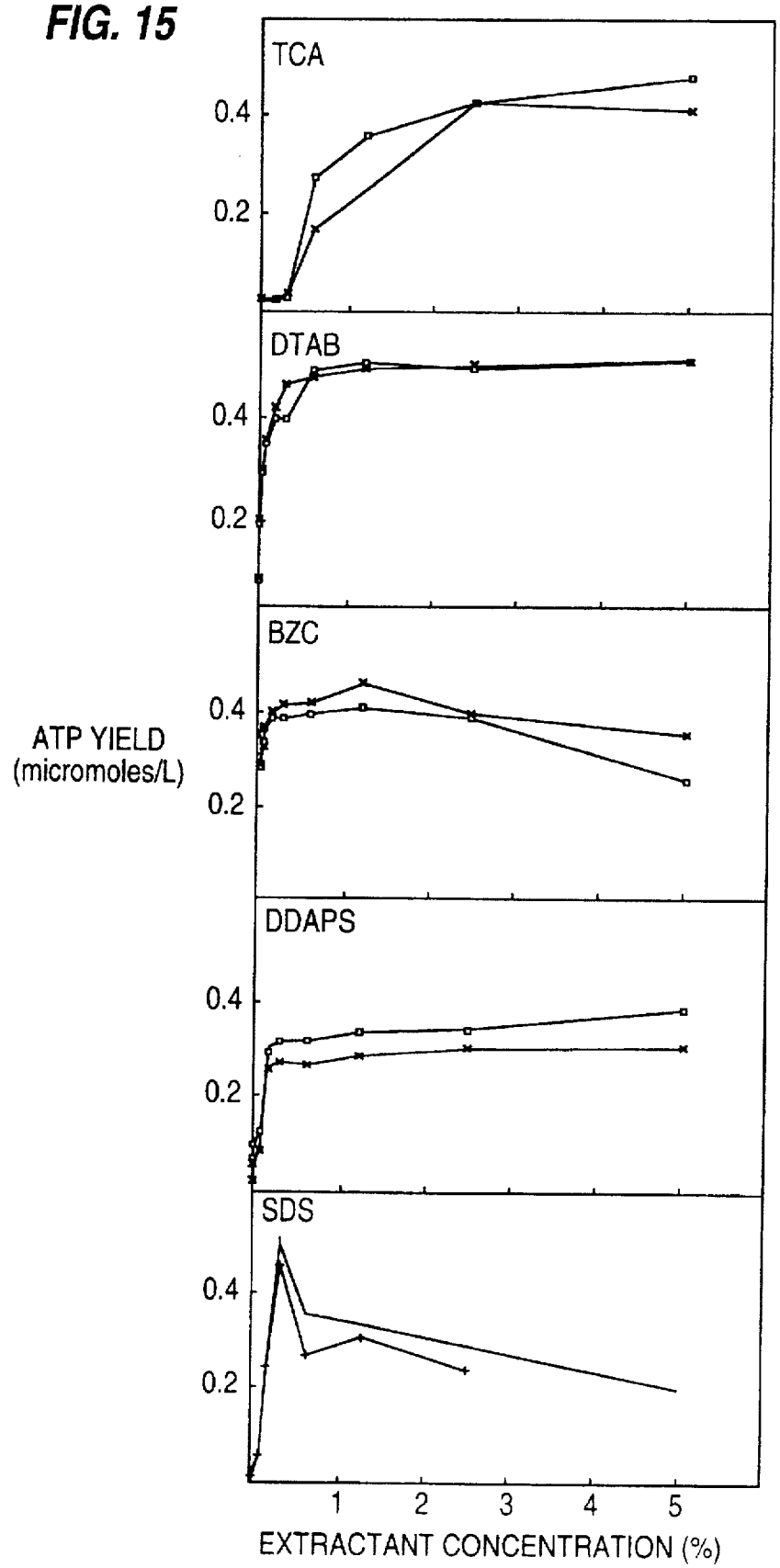
FIG. 15: Effect of extractant concentration on ATP yield in an undiluted culture of Chlorella vulgaris. Extraction times: 1 min (x) and 30 min (□).
Figure 16:
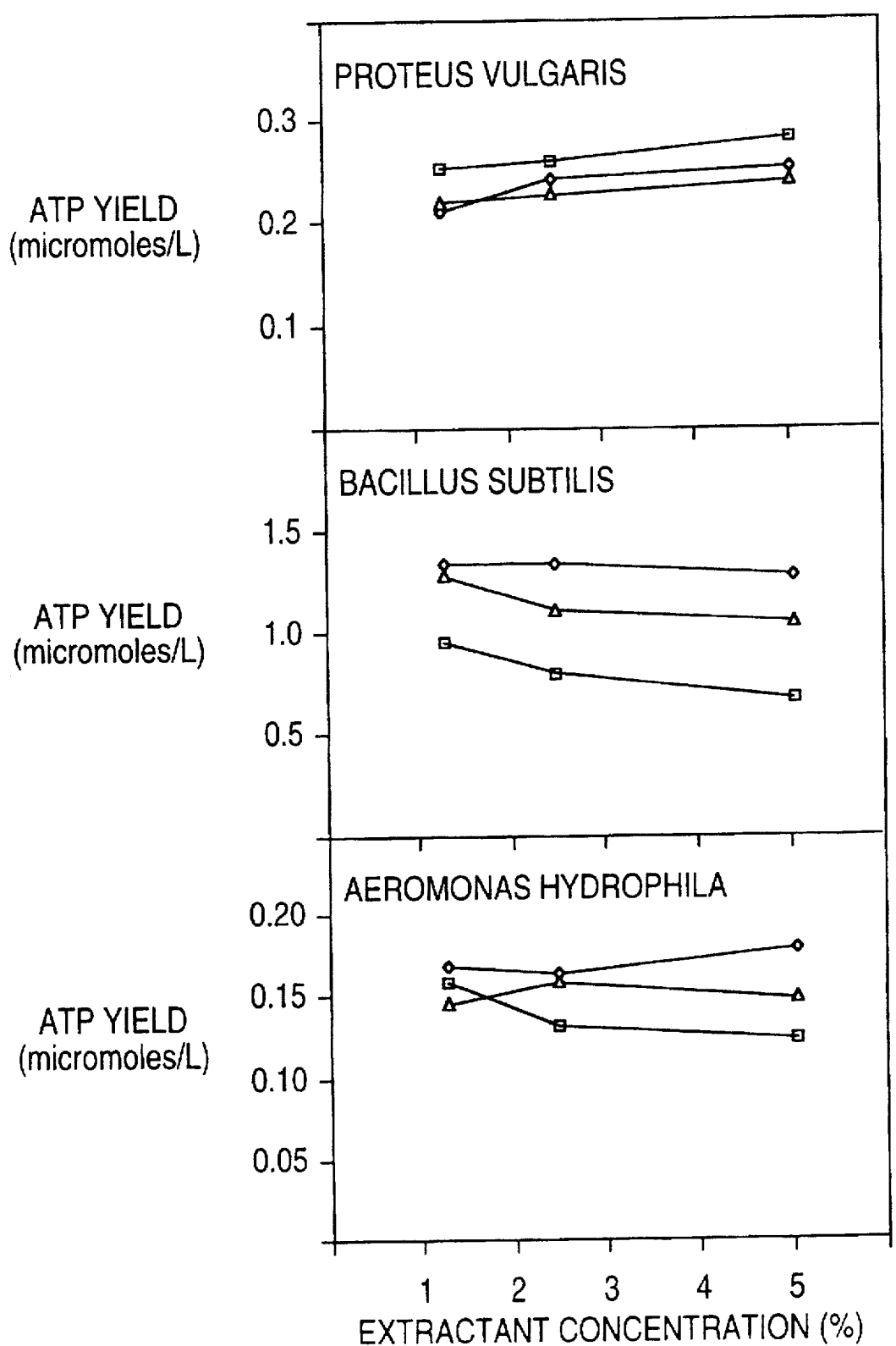
FIG. 16: Yield of ATP in Proteus vulgaris, Bacillus subtilis and Aeromonas hydrophila using various extractants. Over-night cultures of the various strains were 10-fold diluted and aliquots were extracted by mixing with an equal volume of 10, 5 or 2.5% TCA (□), BZC (△) or DTAB (◊) containing 5 mmol/l EDTA. Extracts containing BZC were neutralised by a 4-fold (w/w) amount of βCD. Extracts containing DTAB were neutralised by a 5-fold amount (w/w) of αCD.
Figure 17:
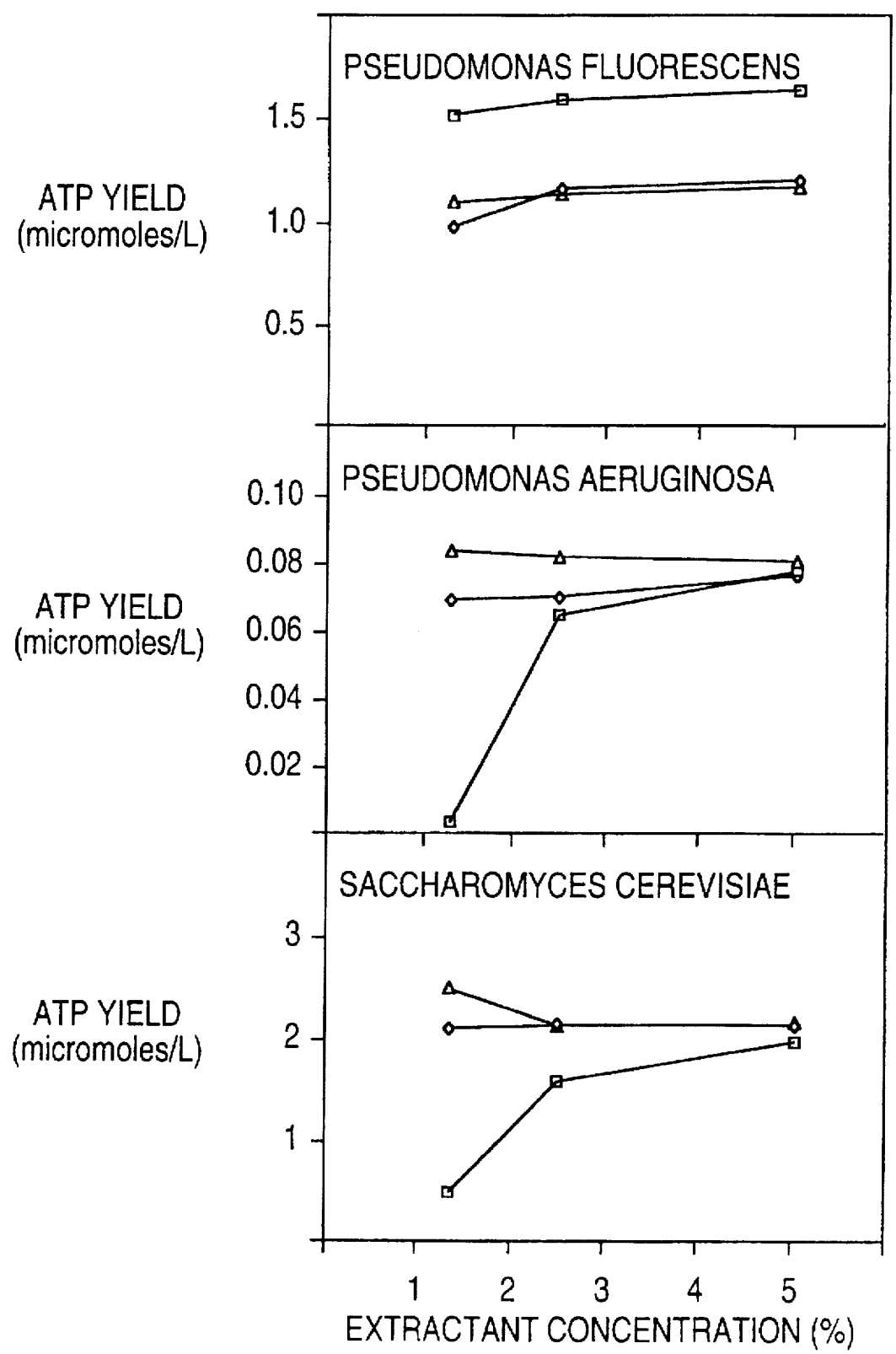
FIG. 17: Yield of ATP in Pseudomonas fluroescens, Pseudomonas aeruginosa and Saccharomyces cerevisiae using various extractants. Extractions and symbols as in FIG. 16.
Figure 18:
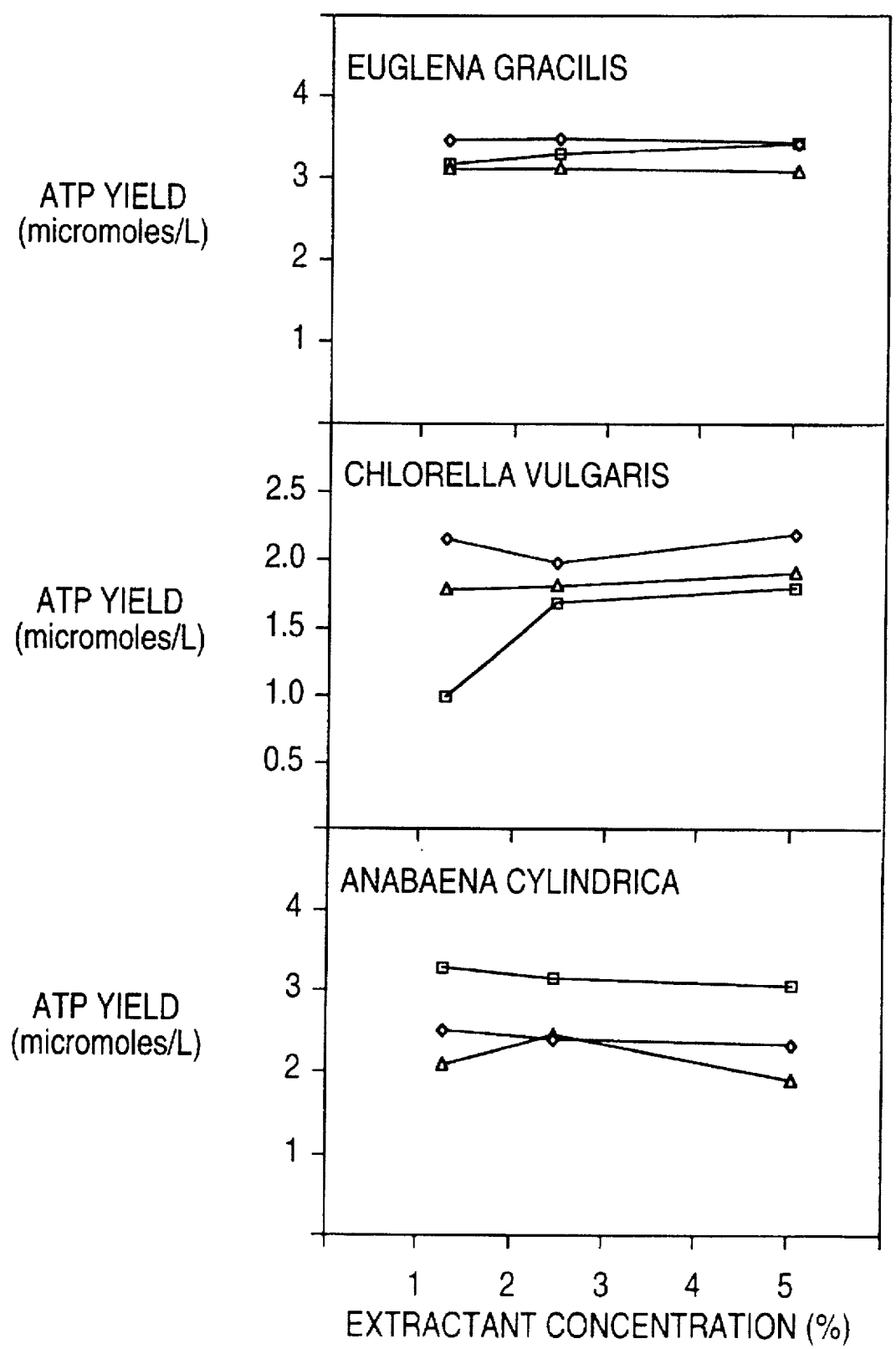
FIG. 18: Yield of ATP in three algal cultures using various extractants. Extractions and symbols as in FIG. 16.
Figure 19:
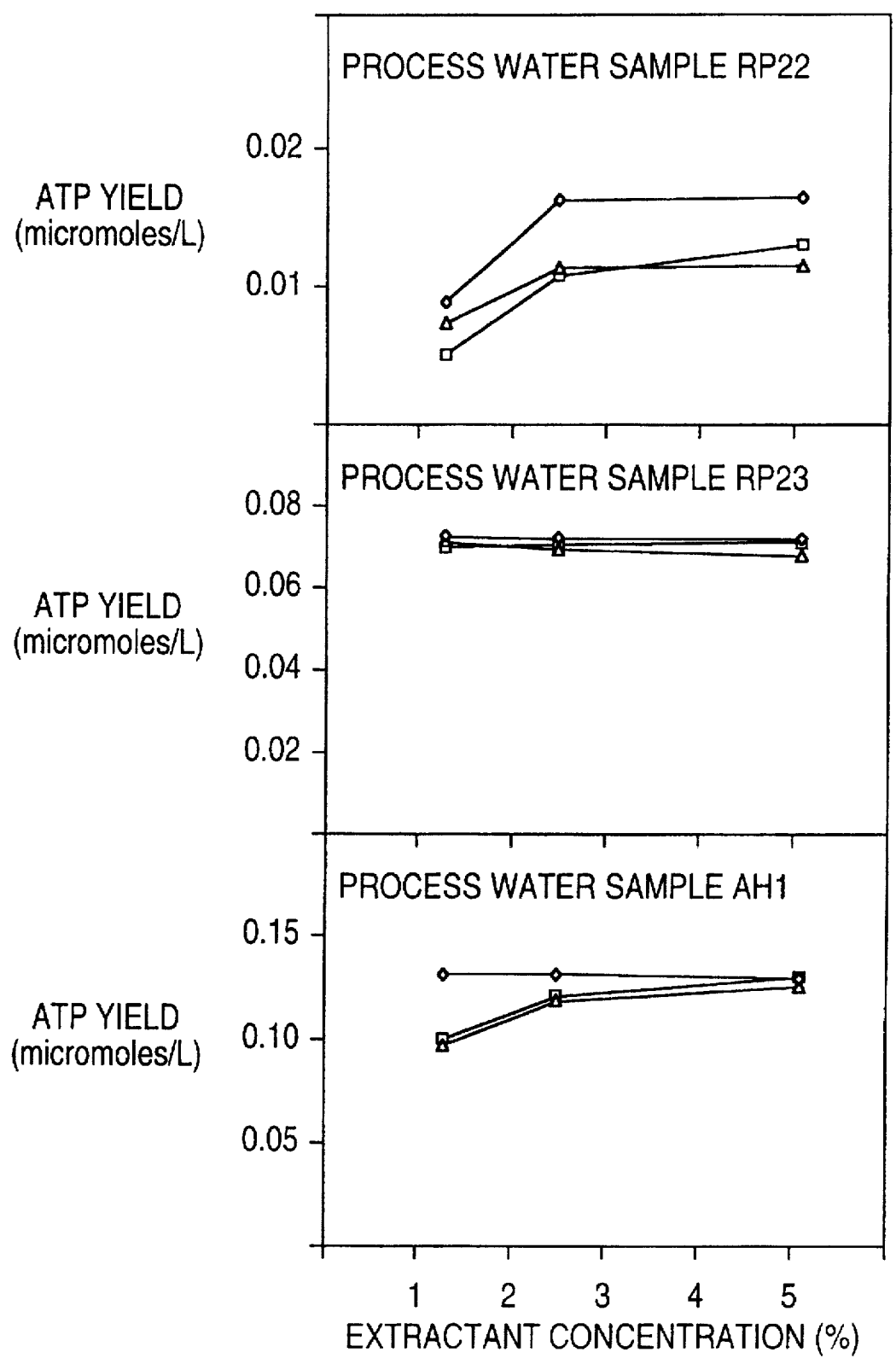
FIG. 19: Yield of ATP in three process water samples using various extractants. Extractions and symbols as in FIG. 16.
Figure 20:
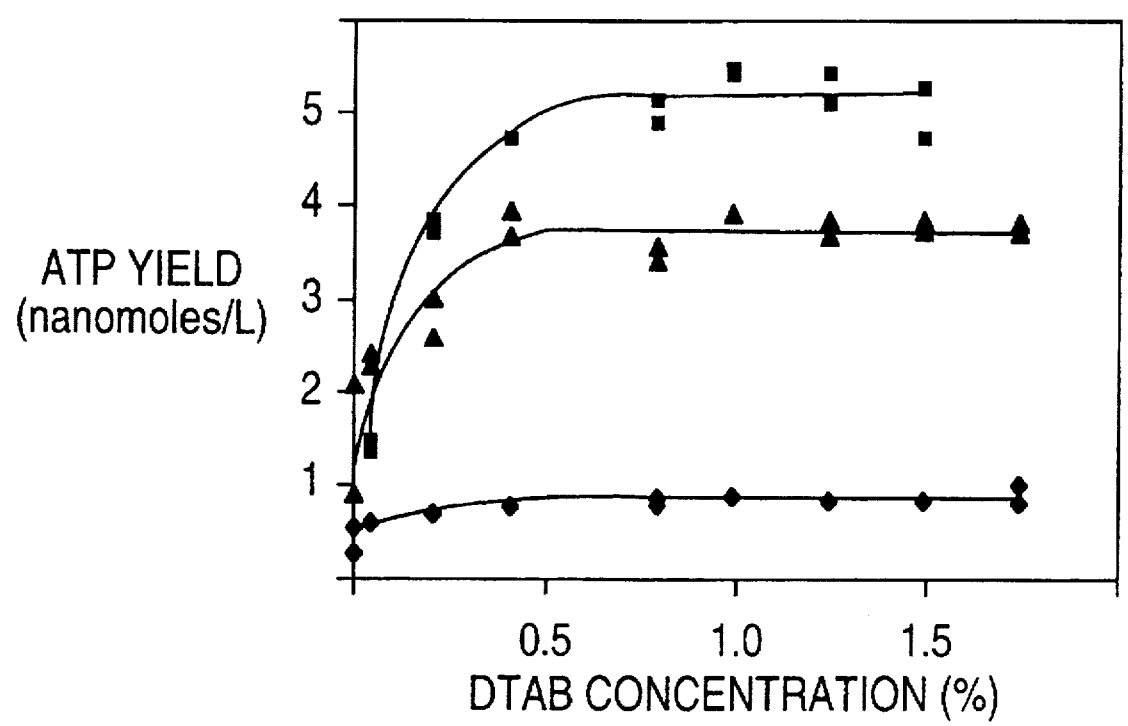
FIG. 20: Yield of ATP in three process water samples extracted with ten different DTAB concentrations. Duplicate measurements are shown using different symbols for the three samples.

Extraction of DNA from Blood via Amplitips

An Amplitip is a pipette tip provided with a membrane of woven polycarbonate fibres at its forward end, marketed by Amersham International plc for extracting components of cells such as high molecular weight genomic DNA.

Red blood cells were lysed with the following buffer to produce nuclei at room temperature for 5-10 min.:

10 mM Tris-pH 8.0
320 mM sucrose
5 mM $MgCl_2$
1% v/v Triton X-100.

An equal volume of the buffer was added to whole blood. Nuclei numbers were determined to be $2.5-3.5 \times 10^6$ nuclei/ml of each sample drawn.

3×125 µl samples were aspirated through Amplitips and then washed sequentially in 2×1 ml phosphate buffered saline, 1 ml distilled water. Each wet tip was dipped into the following buffer for 10-30 seconds:

20 mM Tris pH 8.0
1 mM EDTA pH 8.0
0.5% sodium dodecylsulphate (SDS)
0.4 mg/ml RNase A
40 u/ml RNase T
1 mg/ml proteinase K Each loaded tip was placed carefully in a microcentrifuge tube and incubated in a water bath as follows:

30 mins at 55° C. (protein digestion)
10 mins at 80° C. (proteinase K destruction)

Samples were maintained at room temperature until the restriction enzyme digestion reactions were assembled in the given order:

Total DNA solution 25-35 µl
αCD 10 µl
10×buffer 3 µl
Restriction Enzyme 2 µl

αCD has to be added to the sample to neutralize the detergent prior to the addition of SDS-labile restriction enzyme.

Control DNA samples were included to show the activity of the restriction enzyme stock.

All of the digested material was loaded on to a 1% agarose gel after adding 5 µl 10×loading buffer. Most gels were run overnight and quick blotted the following morning.

Hybridization was performed with human defensin probe (random-primer labeled) with rapid hybridization bugger for 2 hours. Membranes were washed:

Washes: 2×SSC 0.1% SDS 65° C. 15 mins twice
0.1×SSC, 0.1% SDS 65° C. 10 mins twice Autoradiography was performed for 1 to 5 days.

This experiment was repeated with more than 70 different restriction enzymes from the Amersham stock. In each case, the results showed that the α-cyclodextrin had neutralized the extractant to an extent sufficient to permit the restriction enzyme to perform its function.

EXAMPLE 6

Many if not all enzymes are sensitive to phenol contamination being carried over during the extraction process. Exhaustive washing with chloroform and ethanol precipitation is performed to limit the carry-over. The present experiment was performed to test the ability of cyclodextrins to reduce the effect of protein denaturation caused by phenols.

The solubility of three cyclodextrins at 25° was determined to be as follows (g/100 ml):

α-cyclodextrin 14.5
β-cyclodextrin 1.8
γ-cyclodextrin 23.2.

The following formulation was made up to simulate formulations obtained during extraction of DNA from cells:

DNA (IM9) 6 µl (approx. 1 µg)
Restriction buffer 2 µl
Saturated solution of phenol in buffer 5 µl
Cyclodextrin 5 µl
Restriction enzyme 2 µl
Total 20 µl.

The restriction enzymes used were AluI and HaeIII. The formulations were incubated and subjected to agarose gel electrophoresis followed by ethidium bromide staining and visualization on a UV transilluminator.

Each of the three cyclodextrins α-, β- and γ-, were shown to be capable of neutralizing the inhibitory effects on AluI and HaeIII restriction enzymes by low levels of phenol contamination.

The experiment was repeated using successively lower concentrations of α-cyclodextrin. As little as 1 µl of 5% α-cyclodextrin was sufficient to neutralize the effect of 5 µl of the aqueous phase of water saturated with phenol.

EXAMPLE 7

E. coli containing plasmid was grown overnight to a stationary phase and aliquoted into Eppendorf tubes as follows:

| Tube No | |
|---|---|
| 1 | 1 ml culture |
| 2 | 1 ml culture |
| 3 | 100 µl culture |

To each cell pellet, 50 µl of 0.1% SDS was added, briefly vortexed, heated to 100° C. for 1 minute, immediately placed on ice for 1 minute, 50 µl phenol:$CH_3CO$:IAA (24:24:1) added and the mixture vortexed. The mixture was spun for 1 min and 30 µl of aqueous phase decanted. 30 µl of 10% α-cyclodextrin was added to this decanted 30 µl and 10 µl aliquots of each were loaded, cut and uncut into 1% agarose gels and subjected to electrophoresis, ethidium bromide staining and UV visualization.

The results showed that both SDS and phenol could be absorbed by α-cyclodextrin to produce a rapid method of producing plasmid. This has shown that plasmid can be isolated from as little as 100 µl culture.

We claim:

1. In a method of preparing nucleic acids comprising obtaining a sample containing cells and treating said sample with an extractant to lyse said cells and release nucleic acids, the improvement which comprises adding a cyclodextrin to the treated sample to neutralize the extractant.

2. The method as claimed in claim 1, wherein the extractant contains a surfactant.

3. The method as claimed in claim 2, wherein the surfactant is an anionic surfactant.

4. The method as claimed in claim 3, wherein the anionic surfactant is sodium dodecyl sulfonate.

5. The method as claimed in claim 1, wherein the nucleic acid is DNA.

6. The method as claimed in claim 1, wherein the nucleic acid is RNA.

7. The method of claim 1, further comprising enzymatically amplifying or restricting nucleic acids obtained from the treated sample containing cyclodextrin.

8. The method as claimed in claim 7, wherein the further processing is performed in the presence of the cyclodextrin.

9. The method as claimed in claim 1, wherein the cyclodextrin is used in stoichiometric excess over the extractant.

10. The method as claimed in claim 1, wherein the cyclodextrin is α-cyclodextrin.

11. A kit for nucleic acid manipulation comprising an extractant for treating cells to recover nucleic acid therefrom a cyclodextrin for neutralizing the extractant at least one polymerase or restriction enzyme for further processing the recovered nucleic acid by amplification or enzymatic modification or restriction.

12. In a method of preparing nucleic acids comprising obtaining an impure nucleic acid preparation and treating said preparation with phenol, the improvement which comprises adding a cyclodextrin to the treated preparation to neutralize the phenol.

13. The method as claimed in claim 12, wherein the nucleic acid is DNA.

14. The method of claim 12, further comprising enzymatically amplifying or restricting nucleic acids obtained from the treated preparation containing cyclodextrin.

15. The method as claimed in claim 14, wherein the further processing is performed in the presence of the cyclodextrin.

16. The method as claimed in claim 12, wherein the cyclodextrin is used in stoichiometric excess over the phenol.

17. The method as claimed in claim 12, wherein the cyclodextrin is α-cyclodextrin.

* * * * *